US008703484B2

(12) United States Patent
Manson

(10) Patent No.: US 8,703,484 B2
(45) Date of Patent: Apr. 22, 2014

(54) METHODS AND COMPOSITIONS FOR DETECTING IMMUNE RESPONSES

(75) Inventor: Kelledy Manson, Boylston, MA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 929 days.

(21) Appl. No.: 11/913,583

(22) PCT Filed: May 5, 2006

(86) PCT No.: PCT/US2006/017765
§ 371 (c)(1),
(2), (4) Date: Jul. 11, 2008

(87) PCT Pub. No.: WO2006/122050
PCT Pub. Date: Nov. 16, 2006

(65) Prior Publication Data
US 2009/0023174 A1    Jan. 22, 2009

Related U.S. Application Data

(60) Provisional application No. 60/678,329, filed on May 5, 2005.

(51) Int. Cl.
*C12N 5/00*    (2006.01)

(52) U.S. Cl.
USPC .......................................... 435/325; 435/326

(58) Field of Classification Search
USPC ................................................ 435/325, 326
See application file for complete search history.

(56) References Cited

U.S. PATENT DOCUMENTS 6,756,038 B1    6/2004    Schlom et al.

FOREIGN PATENT DOCUMENTS

WO    WO 03/047506 A2    6/2003

OTHER PUBLICATIONS

Watanabe et al. "Immunization of simian immunodeficiency virus-infected rhesus monkeys with soluble human CD4 elicits an antiviral response", PNAS, 1991, 88:4616-4620.*
Schuitemaker et al. "Lack of T cell dysfunction and programmed cell death in human immunodeficiency virus type 1-infected chimpanzees correlates with absence of monocytotropic variants", The Journal of Infectious Diseases, 1993, 168:1140-1147.*
Meinl et al. "Activation of a myelin basic protein-specific human T cell clone by antigen-presenting cells from rhesus monkeys", International Immunology, 1995, 7(9):1489-1495.*
Maue et al. "CD80 and CD86, but not CD154, augment DNA vaccine-induced protection in experimental bovine tuberculosis", Vaccine, 2004, 23:769-779.*
Chackerian et al. "Characterization of a CD4-expressing macaque cell line that can detect virus after a single replication cycle and can be infected by diverse simian immunodeficiency virus isolates", Virology, 1995, 386-394.*
Kantor et al. "Immunogenicity and safety of a recombinant vaccinia virus vaccine expressing the carcinoembryonic antigen gene in a nonhuman primate", Cancer Research, 1992, 52:6917-6925.*
Arlen et al., *Cancer Immunol. Immunother.*, 49: 517-529 (2000).
Arlen et al., *J. of Immunological Methods*, 279: 183-192 (2003).
Beckhove et al., *Blood*, 102(11): 375b (2003).
Hartel et al., *Scand. J. Immunol.*, 49(6): 649-654 (1999).
Kawabuchi et al., *Anticancer Research*, 24: 1193-1200 (2004).
Matsuda et al., *Cancer Immunol. Immunother.*, 53: 609-616 (2004).
Messele et al., *Clinical and Diagnostic Laboratory Immunology*, 7(4): 687-692 (2000).
Palena et al., *Cytokine*, 24: 128-142 (2003).
Parish et al., *J. Immunol. Methods*, 58(1-2): 225-237 (1983).
Plebanski et al., *J. Immunol. Methods*, 170(1): 15-25 (1994).
Sharrock et al., *Immunol. Today*, 11(8): 281-286 (1990).
Sprent et al., *Phil. Trans. R. Soc. Lond. B.*, 355: 317-322 (2000).
Tsang et al., *Clinical Cancer Research*, 10: 2139-2149.
Zaremba et al., *Cancer Research*, 57(20): 4570-4577 (1997).
Manson et al., *Journal of Clinical Oncology*, 24 (18S): 2567 (2006).

* cited by examiner

*Primary Examiner* — Bin Shen
(74) *Attorney, Agent, or Firm* — Leydig, Voit & Mayer, Ltd.

(57) ABSTRACT

The invention provides a method for detecting an antigen-specific hematopoietic cell in a biological sample, wherein the method comprises (a) providing a biological sample comprising a hematopoietic cell of a first species; (b) providing a target cell of a second species, wherein the second species is different from the first species, wherein the second species is a macaque species, and wherein the target cell comprises an antigen; (c) contacting the target cell with the sample; and (d) detecting an immune activation marker or activity in the sample, wherein an increase in expression of the immune activation marker or activity in the sample, relative to a control, is an indication that the sample comprises an antigen-specific hematopoietic cell; and wherein a cell identical to the target cell but lacking the antigen does not stimulate expression of the immune activation marker or activity in hematopoietic cells of the first species.

29 Claims, 15 Drawing Sheets

SEQUENCE LISTING

```
<160> NUMBER OF SEQ ID NOS: 4

<210> SEQ ID NO 1
<211> LENGTH: 9
<212> TYPE: PRT
<213> ORGANISM: Homo sapiens

<400> SEQUENCE: 1

Tyr Leu Ser Gly Ala Asn Leu Asn Leu
 1               5

<210> SEQ ID NO 2
<211> LENGTH: 10
<212> TYPE: PRT
<213> ORGANISM: Homo sapiens
<220> FEATURE:
<223> OTHER INFORMATION: Synthetically generated peptide

<400> SEQUENCE: 2

Ala Thr Trp Gly Gln Asp Val Thr Ser Val
 1               5                  10

<210> SEQ ID NO 3
<211> LENGTH: 8
<212> TYPE: PRT
<213> ORGANISM: Homo sapiens

<400> SEQUENCE: 3

Tyr Ser Gly Ala Asp Leu Asn Leu
 1               5

<210> SEQ ID NO 4
<211> LENGTH: 10
<212> TYPE: PRT
<213> ORGANISM: Homo sapiens

<400> SEQUENCE: 4

Ala Leu Trp Gly Gln Asp Val Thr Ser Val
 1               5                  10
```

METHODS AND COMPOSITIONS FOR DETECTING IMMUNE RESPONSES

RELATED APPLICATIONS

This application is a U.S. National Phase Patent Application of International Patent Application No. PCT/US2006/017765, filed May 5, 2006, which claims the benefit of U.S. Provisional Patent Application No. 60/678,329, filed May 25, 2005, the contents of which are hereby incorporated by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 931 Byte ASCII (Text) file named "702145 Sequence.TXT," created on Oct. 31, 2007.

TECHNICAL FIELD

This invention relates to methods and compositions for detecting immune responses, and more particularly to methods and compositions for detecting cellular immune responses.

BACKGROUND

Methods for monitoring antigen-specific immune responses are important for evaluating the efficacy of immunotherapies such as cancer vaccines. Detection of tumor-specific immune responses can be particularly difficult because tumor antigens are typically self-antigens which are poorly immunogenic. Also, assays in which cell-mediated immune responses are detected in vitro require the use of antigen presenting cells (APC) that are immunologically compatible with the test cells. In other words, in vitro assays to detect antigen-dependent activation of lymphocytes such as T cells employ APC (i) that display major histocompatibility complex antigens (MHC) recognized by antigen receptors expressed on the lymphocyte and (ii) that do not elicit non-specific responses from the lymphocytes.

SUMMARY

Methods and compositions for detecting antigen-specific hematopoietic cells (e.g., antigen-specific lymphocytes) and evaluating immune responses in a subject are provided herein.

In one aspect, the invention features a method for detecting an antigen-specific hematopoietic cell (e.g., an antigen-specific T cell) in a biological sample. The method includes, for example: (a) providing a biological sample comprising a hematopoietic cell of a first species; (b) providing a target cell of a second species, wherein the target cell comprises the antigen; (c) contacting the target cell with the sample; and (d) detecting expression of an immune activation marker or activity in the sample, wherein an increase in expression of the immune activation marker or activity in the sample, relative to a control, is an indication that the sample includes an antigen-specific hematopoietic cell; and wherein a cell essentially identical to the target cell but lacking the antigen does not stimulate expression of the immune activation marker or activity in hematopoietic cells of the first species. The control can be a cell identical to the target cell but which does not comprise the antigen, or a reference value (e.g., a reference level of expression of the immune activation marker or activity).

The antigen can be a tumor-associated antigen (TAA) (e.g., a carcinoembryonic antigen (CEA) or a mucin-1 (MUC-1); a microbial antigen (e.g., a viral, fungal, or bacterial antigen); or a self-antigen associated with an autoimmune condition. In some embodiments, the TAA is a TAA of the first species.

The biological sample can be a sample that includes peripheral blood mononuclear cells (PBMC) or purified subsets thereof (e.g., lymphocytes, e.g., T cells).

In various embodiments, the first species is human and the second species is a primate species (e.g., a macaque species such as rhesus macaque). The target cell can be a cell of a cell line, e.g., an epithelial cell line such as a mammary epithelial cell line.

In some embodiments, the immune activation marker is a cytokine, e.g., selected from IFN-γ, TGF-β, TNF-α, TNF-β, GM-CSF, G-CSF, interleukin-2 (IL-2), IL-3, IL-4, IL-5, IL-6, IL-10, IL-12, and IL-15. In some embodiments, the immune activation marker is a chemokine, e.g., selected from CCL3/MIP-1α, MIP-1β, CCL5/RANTES, XCL1/lymphotactin, and CXCL10/IP-10. In other embodiments, the immune activation marker is a cytotoxin such as granzyme. In other embodiments, the immune activation marker is a cell surface marker for activated hematopoietic cells, e.g., a costimulatory molecule, e.g., B7.1, B7.2, CD152 (CTLA-4), CD28, CD40, CD40 ligand (CD40L), and CD69.

The immune activation marker can be detected with an antibody-dependent assay such as an enzyme-linked immunosorbent assay (ELISA) or an enzyme-linked immunosorbent spot (ELISPOT) assay.

An activity associated with immune activation (e.g., cell proliferation or cytotoxic cell lysis) can be detected in the methods described herein.

In various embodiments, the target cell is infected with a virus that encodes the antigen, e.g., a DNA virus such as a poxvirus. The poxvirus can be an orthopox (e.g., vaccinia or MVA) or avipox (e.g., fowlpox or canarypox).

In various embodiments, the virus further encodes one or more costimulatory molecules of the first species, e.g., one or more of B7.1, LFA-3, and ICAM-1, or all three.

In various embodiments, the target cell is transfected with a nucleic acid that encodes the antigen.

The sample and the target cell can be incubated together at step (c) for at least 24, 48, or 72 hours, or less than 7 days.

In another aspect, the invention features a method for detecting an antigen-specific hematopoietic cell in a biological sample, including: (a) providing a biological sample comprising a hematopoietic cell; (b) providing a target cell of the same species as the hematopoietic cell in (a), wherein the target cell comprises the antigen and wherein the target cell does not express MHC class I molecules; (c) contacting the target cell with the sample; and (d) detecting an immune activation marker or activity in the sample, wherein an increase in expression of the immune activation marker in the sample, relative to a control, is an indication that the sample comprises an antigen-specific hematopoietic cell; and wherein a cell essentially identical to the target cell but lacking the antigen does not stimulate expression of the immune activation marker in hematopoietic cells of the first species. In various embodiments, the target cell does not express MHC class II molecules and/or costimulatory molecules. The control can be a cell identical to the target cell but which does not comprise the antigen, or a reference value (e.g., a reference level of expression of the immune activation marker or activity). The method can further include other features described herein.

In another aspect, the invention features a method of evaluating treatment of a subject. The method includes, for example: (a) obtaining a sample comprising hematopoietic cells from a subject of a first species, wherein the subject is undergoing or being evaluated for an immunotherapeutic treatment for a disease or condition; (b) providing a target cell of a second species, wherein the target cell comprises the antigen; (c) contacting the target cell with the sample; (d) detecting expression of an immune activation marker or activity in the sample, wherein an increase in expression of the immune activation marker or activity in the sample, relative to a control, is an indication that the sample comprises an antigen-specific hematopoietic cell; and wherein a cell essentially identical to the target cell but lacking the antigen does not stimulate expression of the immune activation marker or activity in hematopoietic cells of the first species, thereby evaluating treatment of the subject. The method can further include transmitting the result from the detecting of step (d) to a caregiver. In one embodiment, the caregiver evaluates a further treatment of the subject as a function of the result of the detecting of step (d).

The details of one or more embodiments of the invention are set forth in the accompanying drawings and the description below. Other features, objects, and advantages of the invention will be apparent from the description and drawings, and from the claims.

The term "epitope" refers to the portion of a macromolecule that is specifically recognized by a component of the immune system, e.g., an antibody or T-cell antigen receptor. The term "tumor-associated antigen" or "TAA" refers to a molecule that is differentially expressed in tumor cells relative to non-tumor cells of the same cell type. As used herein, "tumor-associated antigen" includes not only complete tumor-associated antigens, but also epitope-comprising portions (fragments) thereof. A TAA may be one found in nature, or may be a synthetic version of a TAA found in nature, or may be a variant of a naturally-occurring TAA, e.g., a variant that has enhanced immunogenic properties (see, e.g., U.S. Pat. No. 6,756,038 and WO 03/047506).

A "biological sample" encompasses a variety of sample types that are obtained from a subject and can be used in an assay described herein. The term encompasses blood and other liquid samples of biological origin, bone marrow, solid tissue samples such as a biopsy specimen or tissue cultures or cells derived therefrom. The term also includes samples that have been manipulated in any way after their procurement, such as by washing, lysis, fractionation, or treatment with reagents or enrichment for certain cell populations, such as $CD8^+$ T lymphocytes, macrophages, tumor cells, or PBMC.

PBMC were tested for secretion in response to incubation with media, uninfected CMMT 110/C1 cells, and CMMT 110/C1 cells infected with one of the following recombinant viruses: TBC-FPV, rF-TRICOM, PANVAC-F, PROST-VAC®-F.

Figure 11:
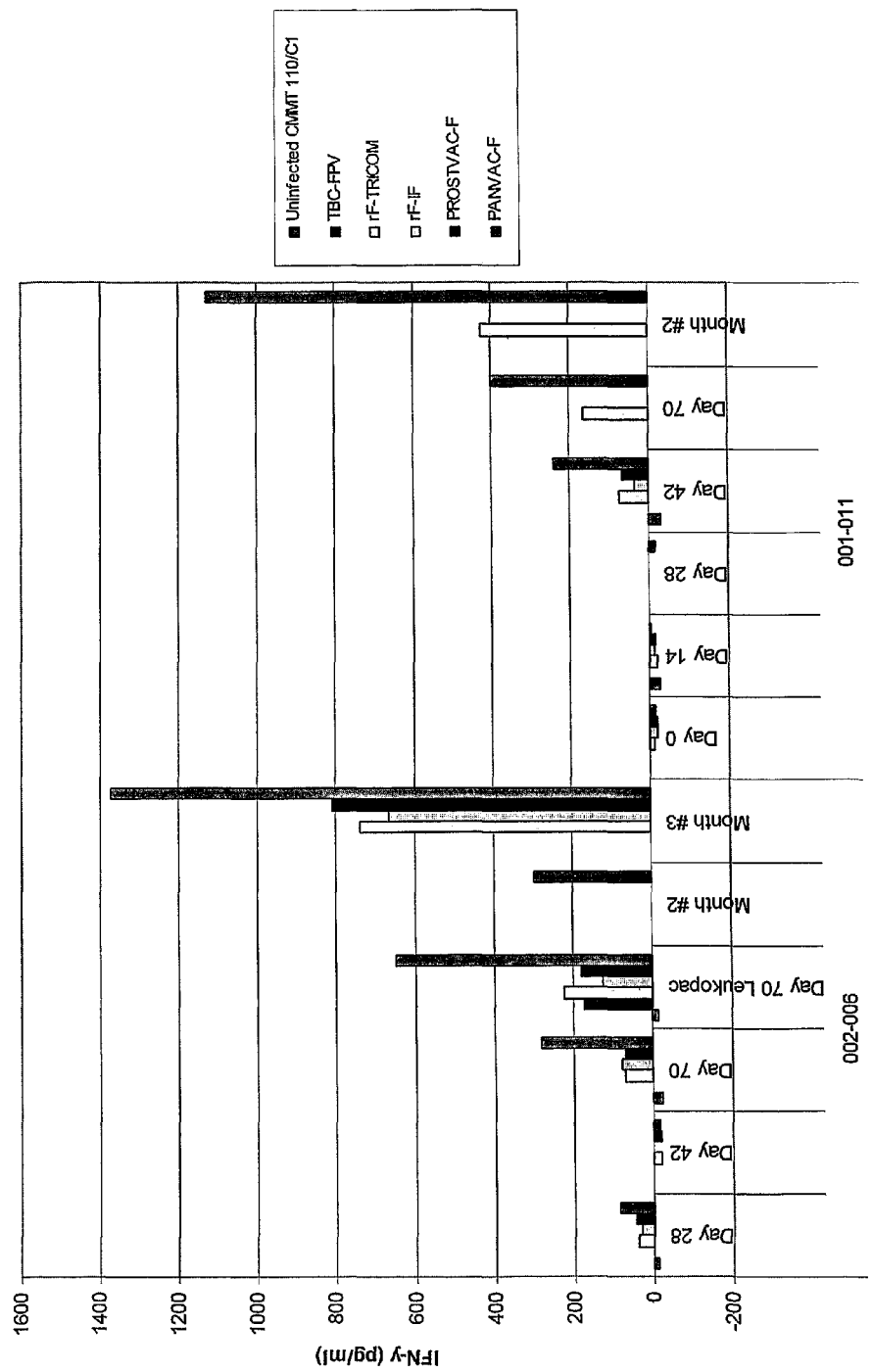

FIG. 11 is a bar graph depicting levels of IFN-γ secreted by PBMC from two HLA-A2⁻ individuals (002-006 and 001-011). PBMC were taken from one patient 28, 42, 70 days, 2 months plus 70 days, and 3 months plus 70 days after initiation of treatment with the PANVAC-VF regimen; from the a second patient 0, 14, 28, 42, 70 days, and 2 months plus 70 days after initiation of treatment with the PANVAC-VF regimen. PBMC were tested for secretion in response to incubation with media, uninfected CMMT 110/C1 cells, and CMMT 110/C1 cells infected with one of the following recombinant viruses: TBC-FPV, rF-TRICOM, rF-IF, PANVAC-F, and PROSTVAC®-F.

Figure 12:
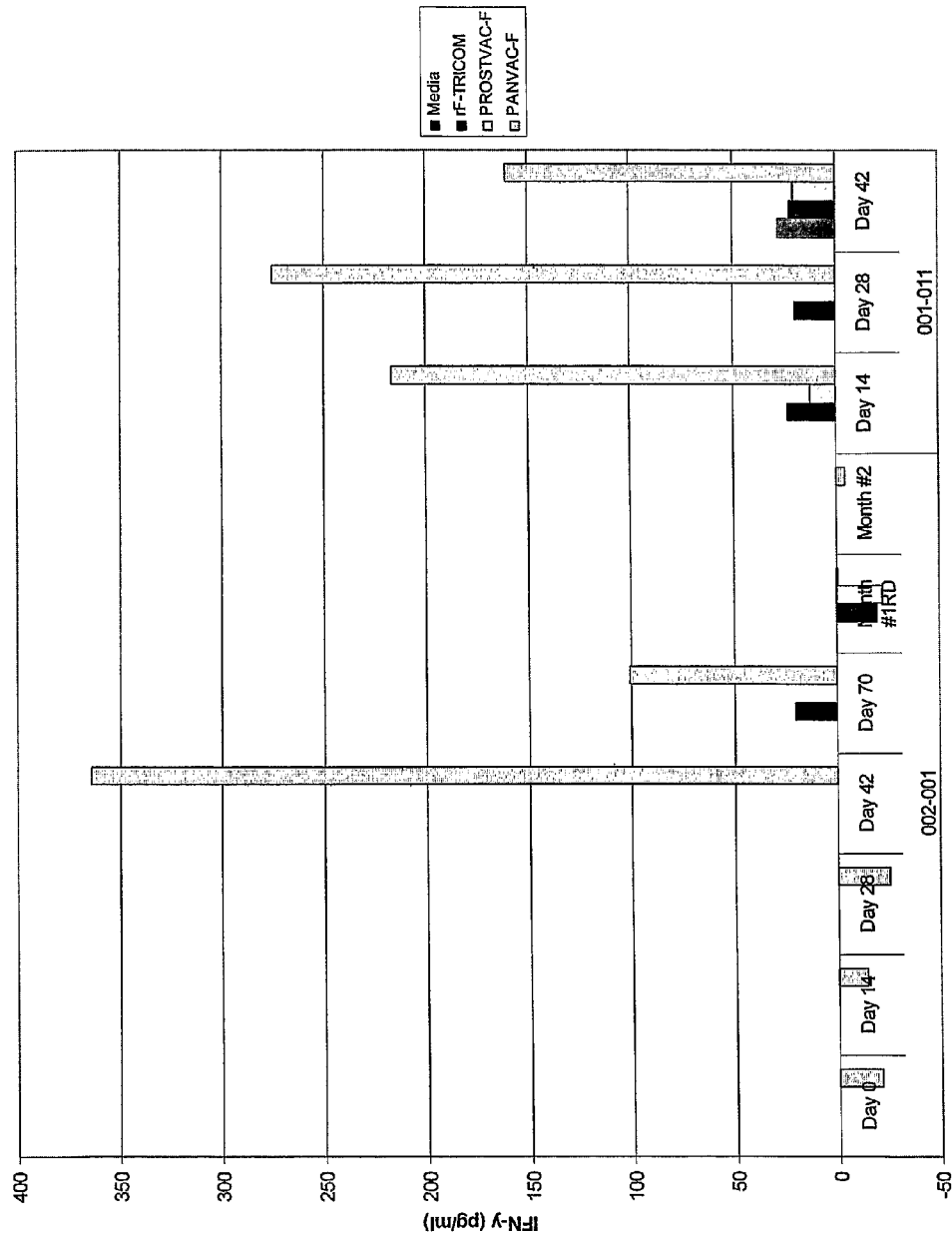

FIG. 12 is a bar graph depicting levels of IFN-γ secreted by PBMC from two HLA-A2⁻ patients (002-001 and 001-011) 0, 14, 28, 42, 70 days, 70 days plus 1 month, and 70 days plus 2 months after initiation of treatment with the PANVAC-VF regimen (or a subset of those time points). PBMC were tested for secretion in response to incubation with media and CMMT 110/C1 cells infected with one of the following recombinant viruses: rF-TRICOM, PANVAC-F, PROSTVAC®-F.

Figure 13:
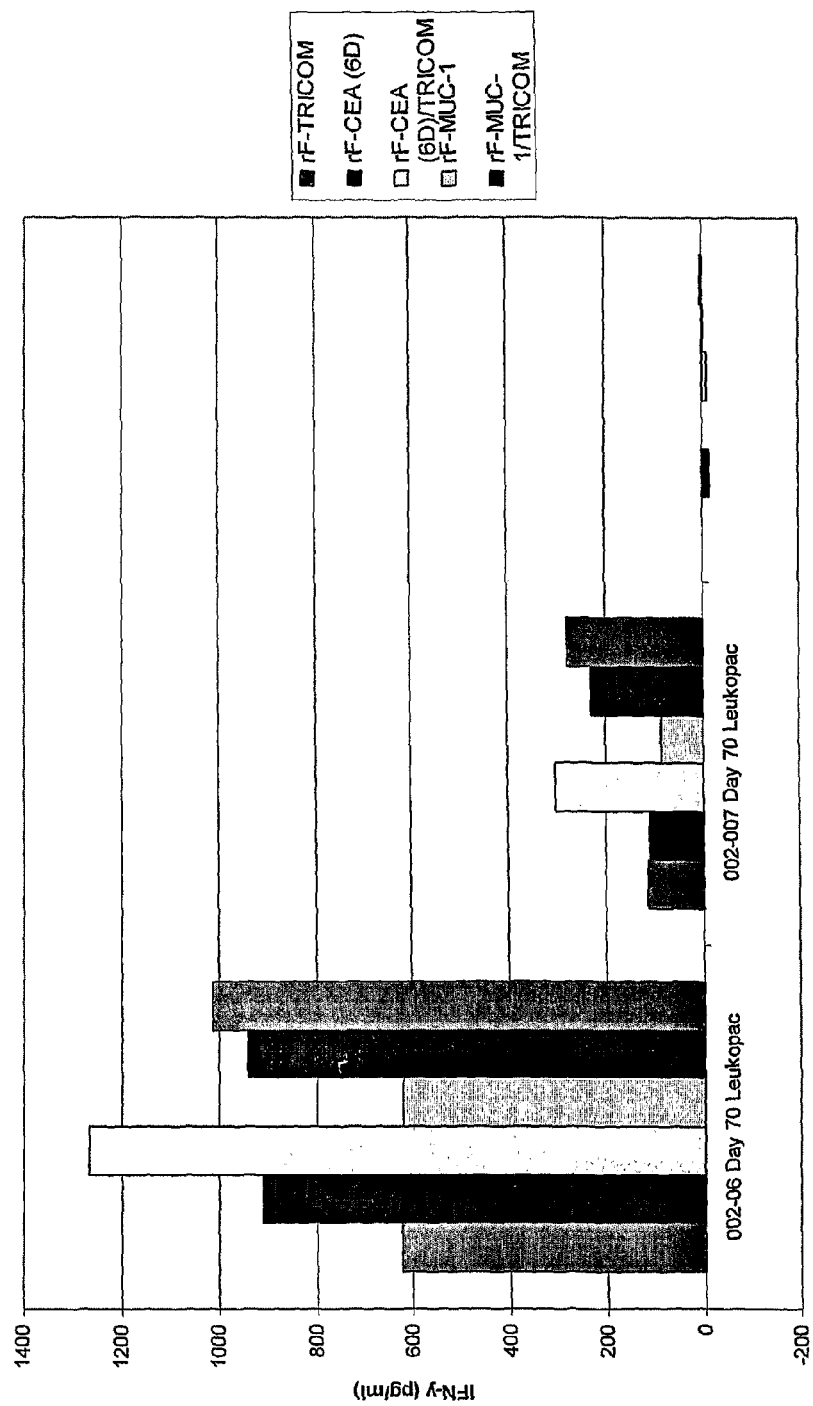

FIG. 13 is a bar graph depicting levels of IFN-γ secreted by PBMC from an HLA-A2⁺ patient (002-007) and an HLA-A2⁻ patient (002-006) 70 days after initiation of treatment with the PANVAC-VF regimen, and by PBMC from a non-vaccinated patient (Naïve Donor). PBMC were stimulated in the presence of CMMT 110/C1 cells infected with the following recombinant viruses: rF-TRICOM, rF-CEA(6D), rF-CEA(6D)/TRICOM, rF-MUC-1, rF-MUC-1/TRICOM, and PANVAC-F.

Figure 14:
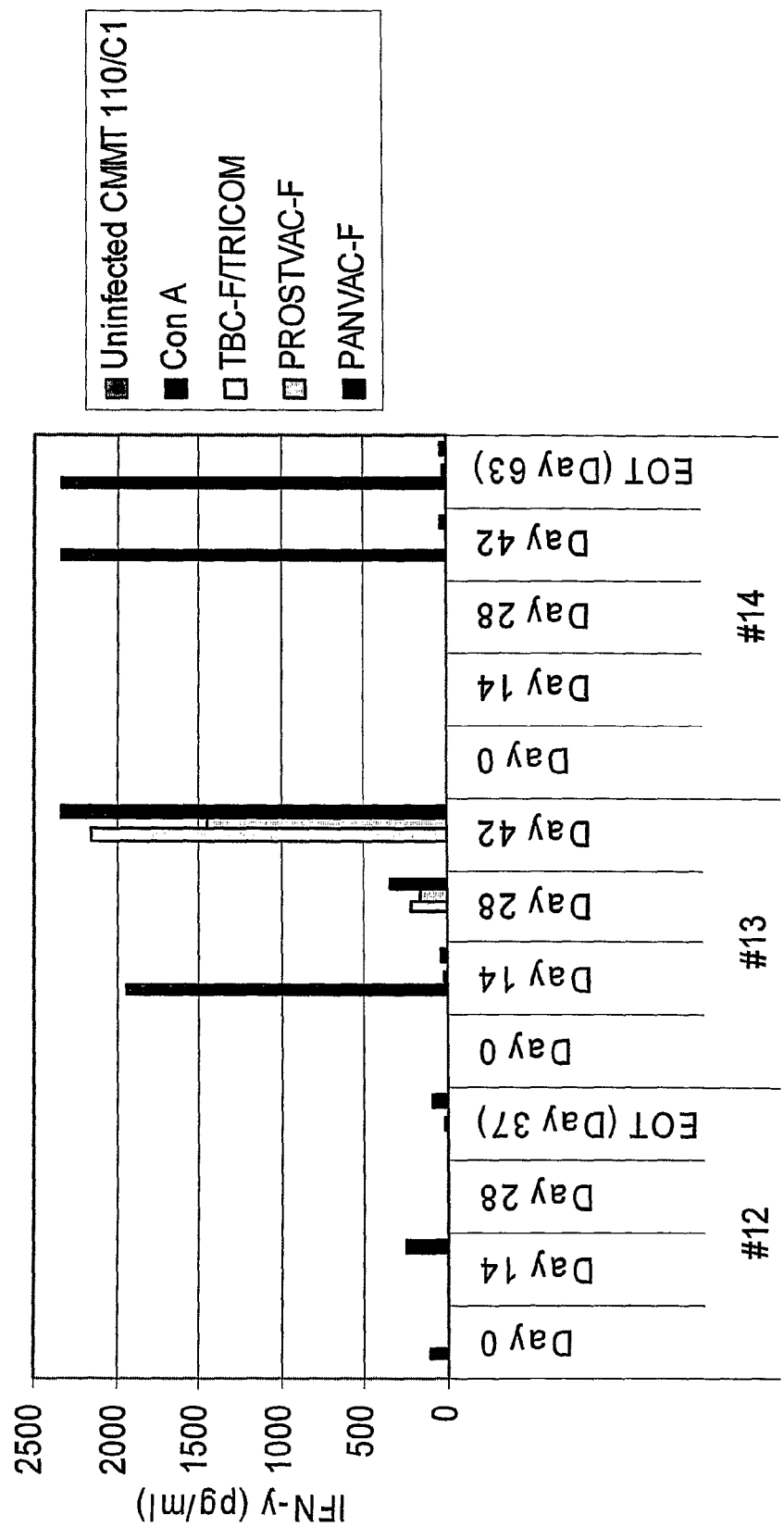

FIG. 14 is a bar graph depicting levels of IFN-γ secreted by PBMC from three different patients (#12, #13, and #14) taken 0, 14, 28, 37, 42, and 63 days (or a subset thereof), after initiation of treatment with the PANVAC-VF regimen. PBMC were stimulated in the presence of uninfected CMMT 110/C1 cells and CMMT 110/C1 cells infected with the following recombinant viruses: rF-TRICOM, PROSTVAC®-F, and PANVAC-F.

Figure 15:
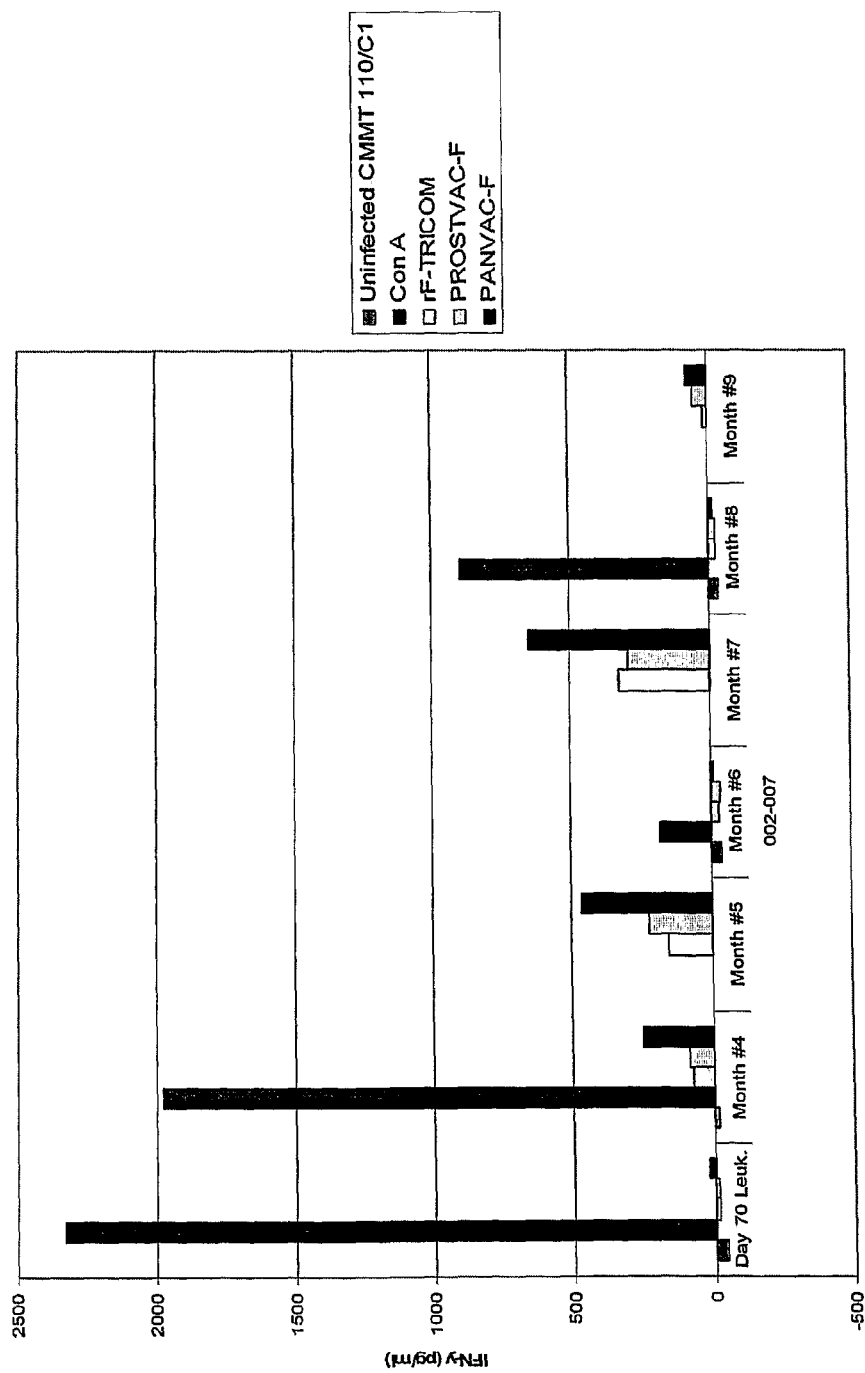

FIG. 15 is a bar graph depicting levels of IFN-γ secreted by PBMC from an HLA-A2⁻ patient (002-007) taken 70 days, and 70 days plus 4, 5, 6, 7, 8, and 9 months after initiation of treatment with the PANVAC-VF regimen. PBMC were stimulated in the presence of uninfected CMMT 110/C1 cells and CMMT 110/C1 cells infected with the following recombinant viruses: rF-TRICOM, PROSTVAC®-F, and PANVAC-F.

Like reference symbols in the various drawings indicate like elements.

DETAILED DESCRIPTION

The methods described herein are based, in part, on the discovery that APC (also referred to as "target cells") expressing an antigen can elicit cell-mediated immune responses in in vitro assays in an MHC-non-restricted manner. The methods employ an APC which does not elicit a non-specific immune response from hematopoietic cells of a subject in the absence of antigen (or, if an immune response is elicited, it is low or undetectable). The APC is treated so as to express the antigen of interest (e.g., by infection or transfection with a recombinant virus or nucleic acid encoding the antigen) and incubated with hematopoietic cells (e.g., PBMC, lymphocytes) in vitro. Responsiveness of the hematopoietic cells to the APC is then evaluated.

Use of APC (and antigens) that elicit responses in an MHC-non-restricted manner in assays are advantageous because the assays do not require previous determination of a subject's MHC genotype. These assays provide an alternative to MHC-restricted cellular assays that employ a target cell (i.e., an APC) of a given, pre-defined MHC genotype. For example, C1R cells are transformed human plasma leukemia cells which do not express endogenous human leukocyte antigen-A (HLA-A) or HLA-B antigens. C1R-A2 cells are stably transfected with a genomic clone of HLA-A2 (described in Arlen et al., *Cancer Immunol. Immunother.*, 49:517-529, 2000). C1R-A2 cells are frequently used as APC in assays to measure patient responses to cancer vaccines. However, these cells are generally used only for testing cells from patients who express HLA-A2, because a patient who does not express HLA-A2 will not exhibit HLA-A2-restricted T cell responses.

It has been discovered that antigen-presenting cells having certain characteristics stimulate antigen-specific responses, regardless of the HLA genotype of the donor. One type of cell which can be used with human hematopoietic cells is CMMT 110/C1 cells. CMMT 110/C1 cells were derived from rhesus monkey mammary gland carcinoma cells obtained from the American Type Culture Collection. As described in further detail in the Examples below, these cells do not elicit immune responses in the absence of antigen. In other words, the MHC, costimulatory molecules (if any) and endogenous antigens expressed by these cells fail to elicit detectable levels of IFN-γ secretion from human PBMC in culture. In this sense, the cells are immunologically "naked" to human PBMC in vitro. CMMT 110/C1 cells infected with recombinant viruses expressing tumor antigens stimulate IFN-γ secretion from PBMC from individuals that have been vaccinated with the same recombinant viruses.

Assay Conditions

Test Cells.

Hematopoietic cells of any subject may be examined by the methods described herein. Mammalian subjects include primate (e.g., human, chimpanzee, macaque), rodent (e.g., mouse, rat, guinea pig, hamster), rabbit, and porcine subjects. PBMC are typically examined in in vitro assays that detect cell-mediated immune (CMI) responses. Other types of samples that may be examined include cells isolated from bone marrow, tissues (e.g., tumor tissues or tissues of a particular organ, e.g., liver), spleen, lymph, cerebrospinal fluid, peritoneum, gut, lung, and secondary lymphoid organs. Purified cells may be provided, such as T cells or natural killer (NK) cells, e.g., isolated from PBMC. Kits for isolation of hematopoietic cell subsets are commercially available. Cells that have been transformed, frozen, and/or propagated in vitro may be assayed as well.

APC/Target Cells.

APC can include any cell type that does not elicit a response (or that elicits a low level of response) from the test cells of interest in the absence of antigen. In one embodiment, the APC can be cells that elicit a response from an antigen-specific lymphocyte in vitro that is at least four times increased in the presence of antigen compared to the response to the APC in the absence of antigen. For example, an APC used to evaluate IFN-γ release by T cells will elicit secretion of quantities of IFN-γ by an antigen-specific T cell that are at least four times greater when the APC expresses the antigen as compared to when the APC which does not express the antigen, e.g., as measured by ELISA for bulk IFN-γ secretion into culture supernatants.

The APC may be from the same species as the test cells, or from a different species. In general, APC of the same species as the test cells that can be used in the methods will express low levels of or no costimulatory molecules. In some embodiments, the APC are negative for expression of MHC molecules (MHC class I and MHC class II molecules). In various embodiments the APC are negative for expression of a costimulatory molecule (e.g., B7.1, B7.2, CD28, CD40, CD40L) and/or are also negative for expression of MHC molecules. The APC also will not express endogenous antigens which are likely to elicit from the test cells a non-specific response that will interfere with detection of the antigen-specific response of interest. For example, APC will be negative for expression of a virus common in the test cell population, wherein the test cell population will include cells that react to the virus. Epstein-Barr Virus (EBV) is common in humans. Therefore, in various embodiments, APC expressing EBV antigens are not be used to evaluate TAA-specific responses in human PBMC, because responses of cells in the PBMC to the EBV antigens will interfere with detection of TAA-specific responses.

APC of a species other than that of the test cells (i.e., xenogeneic APC) can also be used. In one embodiment, xenogeneic APC express low levels or no endogenous MHC and costimulatory molecules. In another embodiment, xenogeneic APC express MHC and costimulatory molecules that do not elicit a non-specific immune response (or elicit a very low level of response) by the test cells in vitro in the absence of antigen (e.g., the response to the APC in the presence of antigen is at least four times as great as the response in the absence of antigen).

In one embodiment, the test cells are human and the APC are from a non-human primate (e.g., ape such as chimpanzee, gorilla, baboon, or monkey such as macaque (e.g., rhesus macaque), lemur, green monkey, or New World monkey species). In one embodiment, the test cells are human and the APC are from a non-primate mammal (e.g., mouse, rat, hamster, rabbit, pig).

The APC used in the present methods may be adherent (e.g., epithelial, fibroblastoid) or non-adherent (e.g., lymphoid) cells. For embodiments in which virus infection will be employed as the means of introducing a DNA encoding a foreign antigen into the APC, the APC must be a cell type permissive for infection with the virus. Transfection of APC with nuleic acid encoding MHC, or otherwise loaded with MHC polypeptides, is not required for the methods described herein.

Antigens.

The methods described herein can be used to detect immune responsiveness, e.g., to TAA or to viral, fungal, parasitic or bacterial antigens. In various embodiments, the antigen is an antigen that includes tandem repeats (such as mucin-1 or carcinoembryonic antigen). These methods can also be used to monitor a subject's immune response against a self-antigen other than a TAA. For example, the methods can be used to detect and/or monitor the progression or prognosis of an autoimmune condition in a subject. Examples of autoimmune conditions include systemic lupus erythematosus, insulin-dependent diabetes mellitus, rheumatoid arthritis, multiple sclerosis, autoimmune hemolytic anemia, autoimmune thrombocytopenic purpura, Goodpasture's syndrome, pemphigus vulgaris, acute rheumatic fever, ankylosing spondylitis, uveitis, Grave's disease, myasthenia gravis, and Hashimoto's thyroiditis. Self antigens associated with these diseases include acetylcholine receptors, thyroid stimulating hormone receptors, platelets, desmoglein-3, Ro protein, insulin receptors, myelin basic protein, proteolipid protein, myelin oligodendrocyte protein, cadherins, Rh blood group antigens, and collagens.

Exemplary TAA include but are not limited to the following: mucin-1 (MUC-1); carcinoembryonic antigen (CEA); prostate-specific antigen (PSA); 707 alanine proline (707-AP); alpha (α)-fetoprotein (AFP); adenocarcinoma antigen recognized by T cells 4 (ART-4); B antigen (BAGE); β-catenin/mutated; breakpoint cluster region-Abelson (Bcr-ab1); CTL-recognized antigen on melanoma (CAMEL); carcinoembryonic antigen peptide-1 (CAP-1); caspase-8 (CASP-8); cell-division cycle 27 mutated (CDC27m); cycline-dependent kinase 4 mutated CDK4/m); cancer/testis (CT) antigen; cyclophilin B (Cyp-B); differentiation antigen melanoma (DAM-6, also known as MAGE-B2, and DAM-10, also known as MAGE-B1); elongation factor 2 mutated (ELF2M); Ets variant gene 6/acute myeloid leukemia 1 gene ETS (ETV6-AML1); glycoprotein 250 (G250); G antigen (GAGE); N-acetylglucosaminyltransferase V (GnT-V); glycoprotein 100 kD (GnT-V); helicase antigen (HAGE); human epidermal receptor-2/neurological (HER-2/neu); HLA-A *0201-R170I (HLA-A*0201 having an arginine (R) to isoleucine (I) exchange at residue 170 of the α-helix of the α2-domain in the HLA-A2 gene); human papilloma virus E7 (HPV-E7); human papilloma virus E6 (HPV-E6); heat shock protein 70-2 mutated (HSP70-2M); human signet ring tumor-2 (HST-2); human telomerase reverse transcriptase (hTERT or hTRT); intestinal carboxyl esterase (iCE); KIAA0205; L antigen (LAGE); low density lipid receptor/GDP-L-fucose: β-D-galactosidase 2-α-L-fucosyltransferase (LDLR/FUT); melanoma antigen (MAGE); melanoma antigen recognized by T cells-1/Melanoma antigen A (MART-1/Melan-A); melanocortin 1 receptor (MC1R); myosin mutated (Myosin/m); melanoma ubiquitous mutated 1 (MUM-1), melanoma ubiquitous mutated 2 (MUM-2), melanoma ubiquitous mutated 3 (MUM-3); New York-esophageous 1 (NY-ESO-1); protein 15 (P15); protein of 190KD bcr-ab1 (p190 minor bcr-ab1); promyelocytic leukaemia/retinoic acid receptor α (Pm1/RARα); preferentially expressed antigen of melanoma (PRAME); prostate-specific membrane antigen (PSM); renal antigen (RAGE); renal ubiquitous 1 (RU1), renal ubiquitous 2 (RU2); sarcoma antigen (SAGE); SART-1; SART-3; translocation Ets-family leukemia/acute myeloid leukemia 1 (TEL/AML1); triosephosphate isomerase mutated (TPI/m); tyrosinase related protein 1 (TRP-1 or gp75); tyrosinase related protein 2 (TRP2); TRP-2/intron 2 (TRP-2/INT2); Wilms' tumor gene (WT-1).

The antigens used in the methods described herein include fragments of full-length polypeptides and/or polypeptides that include mutations relative to the antigen as it is naturally expressed. In one embodiment, the antigen is a CEA (or fragment thereof) which includes an amino acid substitution of Asn to Asp at position 6 in the CAP-1 peptide of CEA. The CAP-1 peptide has the following sequence: YLSGANLNL (SEQ ID NO:1)(Zaremba et al., *Cancer Res.*, 57(20):4570-7, 1997). In one embodiment, the antigen is MUC-1 T2L which includes an amino acid substitution of Thr to Leu at amino acid position 2 of the following fragment of the MUC-1 sequence: ATWGQDVTSV (SEQ ID NO:2)(Tsang et al., *Clin Cancer Res.*, 10(6):2139-49, 2004).

Exemplary bacterial antigens include those associated with human and animal bacterial pathogens including but not limited to *Mycobacterium* spp. (e.g., *Mycobacterium tuberculosis, Mycobacterium leprae*), *Streptococcus* spp. (e.g., *Streptococcus pneumoniae, Streptococcus pyogenes*),

*Staphylococcus* spp. (e.g., *Staphylococcus aureus*), *Treponema* (e.g., *Treponema pallidum*), *Chlamydia* spp., *Vibrio* spp. (e.g., *Vibrio cholerae*), *Bacillus* spp. (e.g., *Bacillus subtilis*, *Bacillus anthracis*), *Yersinia* spp. (e.g., *Yersinia pestis*), *Neisseria* spp. (e.g., *Neisseria meningitides*, *Neisseria gonorrhoeae*), *Legionella* spp., *Bordetella* spp. (e.g., *Bordetella pertussis*), *Shigella* spp., *Campylobacter* spp., *Pseudomonas* spp. (e.g., *Pseudomonas aeruginosa*), *Brucella* spp., *Clostridium* spp. (e.g., *Clostridium tetani*, *Clostridium botulinun*, *Clostridium perfringens*), *Salmonella* spp. (e.g., *Salmonella typhi*), *Borrelia* spp. (e.g., *Borrelia burgdorferi*), *Rickettsia* spp. (e.g., *Rickettsia prowazeki*), *Mycoplasma* spp. (e.g., *Mycoplasma pneumoniae*), *Haemophilus* spp. (e.g., *Haemophilus influenzae*), *Branhamella* spp. (e.g., *Branhamella catarrhalis*), *Corynebacteria* spp. (e.g., *Corynebacteria diphtheriae*), *Klebsiella* spp. (e.g., *Klebsiella pneumoniae*), *Escherichia* spp. (e.g., *Escherichia coli*), and *Listeria* spp. (e.g., *Listeria monocytogenes*). Functional fragments and variants of polypeptides encoded by such pathogens are known in the art and can be expressed by the APC in the methods described herein.

Fungal antigens can be those derived from fungi including but not limited to *Candida* spp. (e.g., *albicans*), *Cryptococcus* spp. (e.g., *neoformans*), *Blastomyces* spp. (e.g., dermatitidis), *Histoplasma* spp. (e.g., *capsulatum*), *Coccidroides* spp. (e.g., *iinmitis*), *Paracoccidroides* spp. (e.g., *brasiliensis*), and *Aspergillus* spp. A bacterial antigen can be an antigen or fragment or variant thereof derived from, e.g., the listed organisms.

Parasitic antigens can be derived from organisms that include but are not limited to *Plasmodium* spp., *Eimeria* spp., *Schistosoma* spp., *Trypanosoma* spp., *Babesia* spp., *Leishmania* spp., *Cryptosporidia* spp., *Toxoplasma* spp., *Pneumocystis* spp., *Entamoeba histolytica*, *Giardia* spp., *Plasmiodium* spp., *Cryptosporidium* spp., *Trichuris trichura*, *Trichinella spiralis*, *Enterobium vermicularis*, *Ascaris lumbricoides*, *Ancylostoma* spp., *Stongyloides* spp., *Filaria* spp., and *Schistosoma* spp. A parasitic antigen can be an antigen or fragment or variant thereof derived from, e.g., the listed organisms.

Expression of Antigens in APC/Target Cells.

The antigen of interest may be expressed by the APC via transfection with a nucleic acid encoding the antigen or via infection with a recombinant virus encoding the antigen. In various embodiments, a recombinant virus (e.g., orthopox such as vaccinia or Modified Vaccinia Ankara (MVA), or an avipox such as fowlpox or canarypox) is used to express the antigen. In various embodiments, the recombinant virus further expresses one or more costimulatory molecules (e.g., costimulatory molecules that interact with ligands on the test cells, e.g., B7.1, LFA-3, or ICAM-1). The combination of B7.1, LFA-3, and ICAM-1 is also referred to as TRICOM™. The conditions for expression by viral infection will depend on the particular APC cell type. Typically, APC will be infected 10-72 hours, e.g., 24 hours, prior to incubation with test cells and washed before being plated with the test cells.

Incubation of Test Cells and APC/Target Cells.

A sample containing test cells is incubated with APC, typically in multiwell culture plates (e.g., 24-well, 48-well, or 96-well plates), in media, under culture conditions appropriate for the cells (e.g., 37° C., 5% $CO_2$) and for an amount of time sufficient for expression of a detectable amount of an immune activation marker by antigen-specific cells, or for an antigen-dependent biological event (e.g., cytotoxic lysis of APC), in the sample (e.g., 6 hours, 12 hours, 1 day, 2 days, 3 days, 4 days, 5 days, 6 days, 7 days, 10 days, or longer). Optimal ratios of test cells:APC can be determined empirically, and will generally be in the range of 1:1, 2:1, 5:1, 10:1, or 25:1. Cells and/or culture supernatants are then examined to evaluate the quantity and/or quality of immune activation markers. Additional preparation steps may be required for assays in which cytotoxic lysis or ELISPOT analyses are to be performed. These are discussed in the section below.

Detection of Immune Responses

Antigen-specific immune responses elicited in the assays can be detected by art-known methods. Expression of immune activation markers on test cells or in the culture supernatants can be examined. Alternatively, or in addition, immune responsiveness is examined by evaluating cytotoxic lysis of antigen presenting cells.

Immune Activation Markers.

Many molecules have been identified as indicative of antigen-specific immune activation. These molecules, or markers, include soluble mediators (e.g., cytokines, chemokines), cell-surface molecules that are upregulated under conditions of immune activation (e.g., costimulatory molecules, adhesion molecules), and toxic mediators produced by immune effector cells (e.g., cytotoxins such as granzymes). Cytokines produced by T cells, NK cells, and other immune effector cells (e.g., macrophages, monocytes, B cells, neutrophils, eosinophils, basophils) which may be assayed in the present methods include: IFN-γ, TGF-β, TNF-α, TNF-β, GM-CSF, G-CSF, interleukin-2 (IL-2), IL-3, IL-4, IL-5, IL-6, IL-10, IL-12, and IL-15. Chemokines that may be assayed include: CCL3/MIP-1α, MIP-1β, CCL5/RANTES, XCL1/lymphotactin, and CXCL10/IP-10. Cell surface markers indicative of activation include B7.1, B7.2, CD152 (CTLA-4), CD28, CD40, CD40 ligand (CD40L), and CD69.

ELISA.

Enzyme-linked immunosorbent assays (ELISA) are useful for detecting soluble mediators such as cytokines. In one embodiment, supernatants are collected from test cell/APC incubation assay samples and levels of cytokine released in the supernatants are quantitated by ELISA. For a description of ELISA methods for detecting cytokines see, e.g., U.S. Pat. No. 6,218,132.

ELISPOT.

Enzyme-linked immunosorbent spot (ELISPOT) assays detect cytokine release on a single-cell basis. Typically, test cells and APC are incubated in a culture plate that has been coated with antibody that specifically binds to the cytokine of interest. After test cells and APC are incubated together for the desired length of time, cells are lysed in the wells. A second antibody that recognizes the cytokine of interest is added to the plates to bind to cytokine that has been captured by the plate-bound antibody, and is subsequently detected by secondary reagents, that reveal spots where individual cells secreted cytokine. For a detailed protocol for detecting cytokine secretion by ELISPOT, see, e.g., Arlen et al., *Cancer Immunol. Immunother.*, 49:517-529, 2000.

Proliferative and Cytotoxic Cellular Responses.

Cytotoxic responses (e.g., T cell- or NK-cell mediated cytotoxic responses) are one type of immune activity that can be evaluated in the methods described herein. These can be measured by any suitable technique, e.g., chromium release assays. Proliferative responses of hematopoietic cells can also be evaluated, e.g., by a mixed lymphocyte reaction (MLR). Briefly, target cells are irradiated and co-cultured with test cells in microtiter culture plates for ~5 days. During the last 8 hours of the culture period, the cells are pulsed with 1 μCi/well of $^3$H-thymidine, and the cells are harvested for counting onto filter paper by a cell harvester. $^3$H-thymidine incorporation is measured by standard techniques. Proliferation of cells in such assays is expressed as the mean counts per minute (cpm) read for the tested wells. Limiting dilution analysis (LDA) is another method by which to evaluate the frequency of antigen-specific lymphocytes in a sample. Guidance and principles related to T cell proliferation assays are described in, e.g., Plebanski and Burtles, *J. Immunol. Meth.* 170:15, 1994; Sprent et al., *Philos. Trans R. Soc. Lond. B. Biol. Sci.*, 355(1395):317-22, 2000; and Messele et al., *Clin. Diagn. Lab. Immunol.*, 7(4):687-92, 2000. LDA is described in, e.g., Sharrock et al., *Immunol. Today*, 11:281-286, 1990. Other lymphocyte analytical techniques are described in Hartel et al., *Scand. J. Immunol.*, 49(6):649-54, 1999 and Parish et al., *J. Immunol. Methods*, 58(1-2):225-37, 1983.

Diagnostics and Patient Care

The methods described herein can be used for diagnostic purposes, e.g., in patient care. For example, the methods can be used in evaluating a subject. The subject can be healthy or suffering from a disease. In various embodiments, the subject is a patient undergoing treatment (e.g., vaccination and/or immunotherapy) for a malignant disease, e.g., a cancer such as a pancreatic cancer or a prostate cancer. In one embodiment, the method includes: obtaining a sample comprising hematopoietic cells from a subject, e.g., from a caregiver, e.g., a caregiver who obtains the sample from the subject; determining whether the sample includes antigen-specific hematopoietic cells, e.g., by a method described herein. The subject can be a subject that has been exposed to an antigen (either naturally exposed or exposed via vaccination or immunotherapy), or a subject who is naïve to the antigen. Samples can be obtained from the subject one, two, three or more times over a period of time in order to evaluate responsiveness to a vaccine or immunotherapy regimen. Data obtained from the methods in which the samples are evaluated can be compared with other data regarding the subject, e.g., a clinical parameter such as tumor progression or incidence of an infectious disease or a symptom associated with an infectious disease.

In various embodiments, data obtained from a method in which a sample is taken from a subject and evaluated for immune responsiveness is transmitted to a caregiver. The caregiver may make a decision regarding further treatment of the subject based on the data transmitted.

EXAMPLES

Example 1

Comparison of ELISPOT and Cytokine Secretion Assays to Detect Tumor-Specific Immune Cells The following assays were performed to test a patient's responsiveness to treatment with the PANVAC-VF regimen, a therapeutic vaccination regimen for pancreatic cancer patients. The regimen involves the sequential use of a recombinant vaccinia virus (PANVAC-V) and a recombinant fowlpox virus (PANVAC-F) as vaccines. Each of the two recombinant viruses contains sequences encoding five proteins: CEA, mucin-1 (MUC-1), B7.1, Intercellular Adhesion Molecule-1 (ICAM-1), and Lymnphocyte Function-associated Antigen-3 (LFA-3). Patients treated with the PANVAC-VF regimen received a priming dose of $2\times10^8$ plaque forming units (pfu) of PANVAC-V subcutaneously on day 0, followed by a boost dose of $1\times10^9$ pfu PANVAC-F subcutaneously on days 14, 28, and 42. Recombinant GM-CSF (100 µg) was administered at the injection site on the day of each vaccine administration and for three consecutive days thereafter. PBMC were collected from patients at time points after initiation of treatment and frozen for assays.

The patient tested in this assay, patient #7 (002-007), expresses HLA-A2. Therefore patient #7's PBMC were tested for responsiveness to target cells expressing HLA-A2. The HLA-A2-expressing target cells chosen for this assay were C1R-A2 cells. PBMC were also tested in a non-restricted assay in which CMMT 110/C1 cells were used as target cells.

To prepare the patient's PBMC for the assays, they were thawed, resuspended in Animal Media (RPMI with 10% fetal bovine serum, L-glutamine, antibiotics, and β-mercaptoethanol), counted, and incubated overnight at 37° C., 5% $CO_2$. Next, PBMC were incubated in culture in 24-well plates with target cells and/or antigen for 72 hours. A 1:1 ratio of PBMC: target cells ($1\times10^6$ PBMC: $1\times10^6$ target cells per well) was used for all culture conditions. Incubations with the following combinations of PBMC and target cells and/or antigens were performed:

PBMC+Media
PBMC+Con A
PBMC+Vaccinia Lysate (TBC-Wyeth)
PBMC+C1R-A2
PBMC+C1R-A2 pulsed with CAP-1-6D
PBMC+C1R-A2 pulsed with MUC-1 T2L peptide
PBMC+CMMT 110/C1
PBMC+CMMT 110/C1 infected with TBC-FPV (MOI=10)
PBMC+CMMT 110/C1 infected with rF-CEA/TRICOM (MOI-10)
PBMC+CMMT 110/C1 infected with rF-MUC-1/TRICOM (MOI=10)

Con A is concanavalin A, a polyclonal T cell mitogen derived from Jack beans. CAP-1-6D is a peptide from human carcinoembryonic antigen (CEA)(American Peptide Co., cat. no. 30341) with the following sequence: YSGADLNL (SEQ ID NO:3). The MUC-1 T2L peptide has the following sequence: ALWGQDVTSV (SEQ ID NO:4)(American Peptide Co.). This peptide has a Thr to Leu substitution at position 2 relative to the corresponding peptide within the wild-type MUC-1 sequence. C1R-A2 cells were pulsed with 10 µg/ml of each peptide.

TBC-FPV is a fowlpox virus that does not encode any tumor antigens or human costimulatory molecules. rF-CEA/TRICOM is a recombinant fowlpox virus derived from TBC-FPV and that expresses CEA and TRICOM. rF-MUC-1/TRICOM is a recombinant fowlpox virus derived from TBC-FPV and that expresses MUC-1 and TRICOM.

CMMT 110/C1 cells were infected 24 hours before culture with PBMC and washed immediately before plating with PBMC. After the incubation, cells were harvested and counted to perform ELISPOT assays as described in Arlen et al., *Cancer Immunol. Immunother.*, 49:517-529, 2000. Briefly, harvested cells were counted and plated ($2\times10^5$ total cells/well) on an ELISPOT assay plate pre-blocked with complete (i.e., serum-containing) medium. Cells were incubated overnight at 37° C. for 34 hours; plates were washed six times with phosphate buffered saline-Tween20 (PBS-Tween20); and 100 µl of biotinylated anti-IFN-γ antibody (2 µg/ml; Pharmingen, cat. no. 554550) in PBS with 1% bovine serum albumin (BSA) was added to each well. Plates were incubated at 4° C. overnight, washed three times with PBS, and incubated with avidin alkaline phosphatase (Southern Biotechnology Assoc., cat. no. 7100-04) at a 1:2000 dilution for two hours at room temperature. Plates were washed three times with PBS, incubated with KPL BCIP/NBT (5-Bromo-6-Chloro-3-indoylphosphate p-Toluidine Salt/Nitro-Blue Tetrazolium Chloride) phosphatase substrate for 30-60 minutes and washed with distilled, deionized water. The plastic bottoms were removed from the plates, rinsed and dried, and spots were counted.

The Con A and vaccinia lysate conditions produced high numbers of spots in the assays, as expected. The media condition displayed few or no spots. High levels of spots were observed in all wells in which C1R-A2 cells were used, indicating lack of specificity of a response. Very few spots were seen in samples containing CMMT 110/C1 cells.

Figure 1:
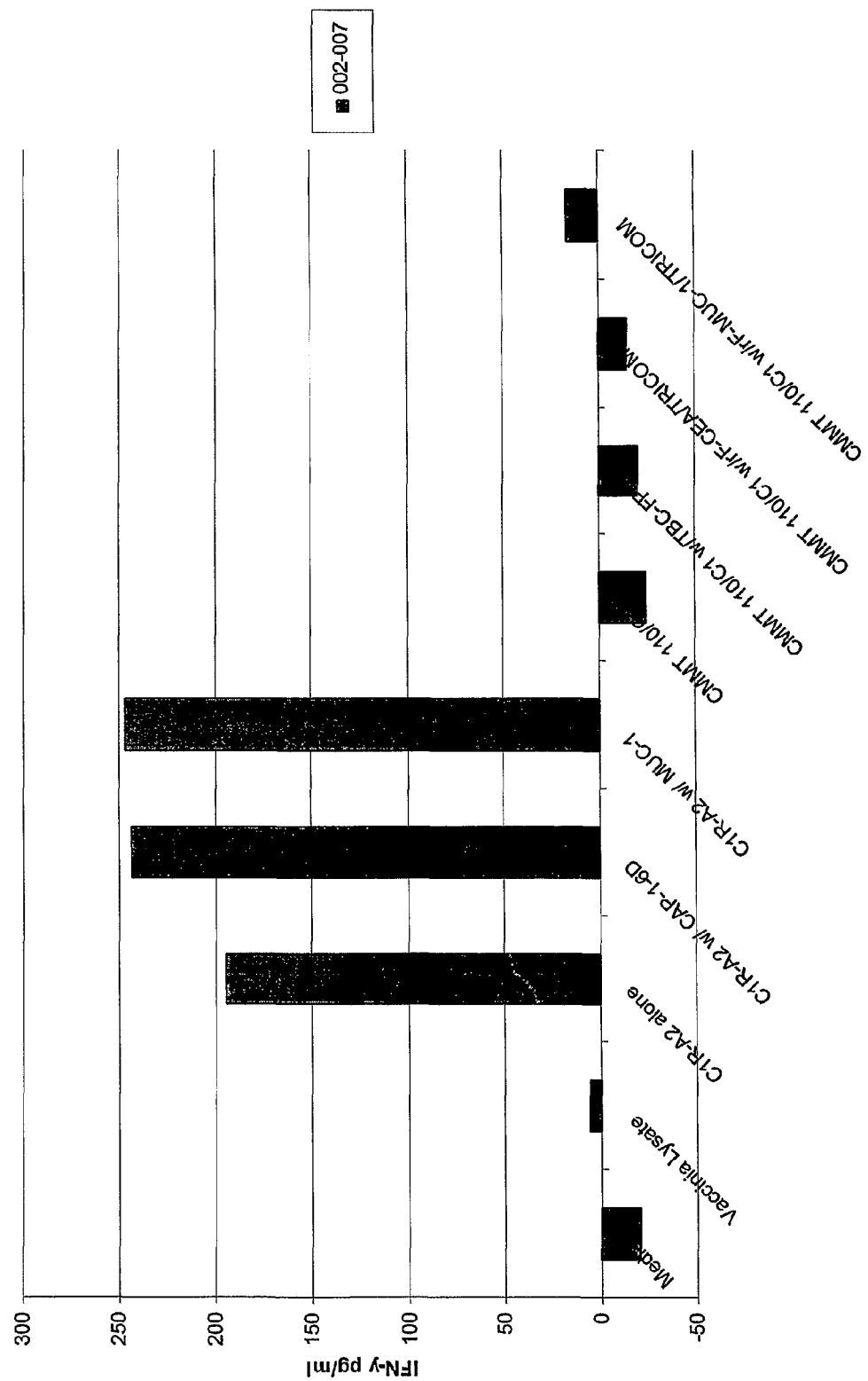
FIG. 1 is a bar graph depicting levels of IFN-γ secreted by PBMC obtained from an HLA-A2$^+$ patient (002-007) 70 days after initiation of treatment with the PANVAC-VF regimen. PBMC were stimulated in the presence of media, vaccinia lysate, C1R-A2 cells alone or pulsed with CAP-1-6D peptide or the MUC-1 T2L peptide, CMMT 110/C1 cells alone or transfected with TBC-FPV, rF-CEA, or rF-MUC-1.

IFN-γ secretion was determined by performing IFN-γ ELISA assays using a Human IFN-γ Immunoassay Kit (R&D Systems Inc., Minneapolis, Minn.; catalog no. DIF50 or SIF50). Culture supernatants were examined by ELISA both neat and at 1:100 dilution. The results from the ELISA assays with undiluted supernatants are plotted in FIG. 1. ConA samples were excluded from the graph because the levels of IFN-γ were too high to be accurately measured. As shown in FIG. 1, all conditions other than those that included C1R-A2 cells showed low or negative responses. The non-specific responsiveness to C1R-A2 cells is thought to be due to reaction of the PBMC to EBV antigens expressed by the C1R-A2 cells.

Example 2

HLA-A2$^+$ and HLA-A2$^-$ Cells Respond to Antigens Presented by Macaque Cells

The following assays were performed to examine responsiveness of two patients receiving the PANVAC-VF regimen; an HLA-A2$^+$ patient, #7, and an HLA-A2$^-$ patient, #6 (002-006). PBMC of a non-vaccinated individual (Naïve Donor) were examined in parallel. The assays were performed as described in Example 1, above. Incubations with the following combinations of PBMC and target cells and/or antigens were performed:
PBMCs+Media
PBMCs+Con A
PBMCs+Vaccinia Lysate
PBMCs+C1R-A2s
PBMCs+C1R-A2s pulsed with CAP-1-6D peptide
PBMCs+C1R-A2s pulsed with MUC-1 T2L peptide
PBMCs+CMMT 110/C1
PBMCs+CMMT 110/C1 infected with TBC-FPV
PBMCs+CMMT 110/C1 infected with rF-CEA/TRICOM
PBMCs+CMMT 110/C1 infected with rF-MUC-1/TRICOM
PBMCs+CMMT 110/C1 infected with PANVAC-F (sample 1)
PBMCs+CMMT 110/C1 infected with PANVAC-F (sample 2)

CMMT 110/C1 cells were infected with viruses at a MOI of 40. For certain conditions, CMMT 100/C1 cells were also infected at a MOI of 10. CMMT 110/C1 cells infected with two different samples of PANVAC-F.

ELISPOT assays were performed as described in Example 1. The results of the vaccinia, Con A, and media conditions in which patient #7 and #6 PBMC samples were used were positive, positive, and negative, respectively, as expected. The results in which C1R-A2 cells were used exhibited high levels of background compared to assays in which C1R-A2 cells were incubated alone, as a negative control. No uniform results were observed in CMMT 110/C1 assays when measured by ELISPOT.

Figure 2:
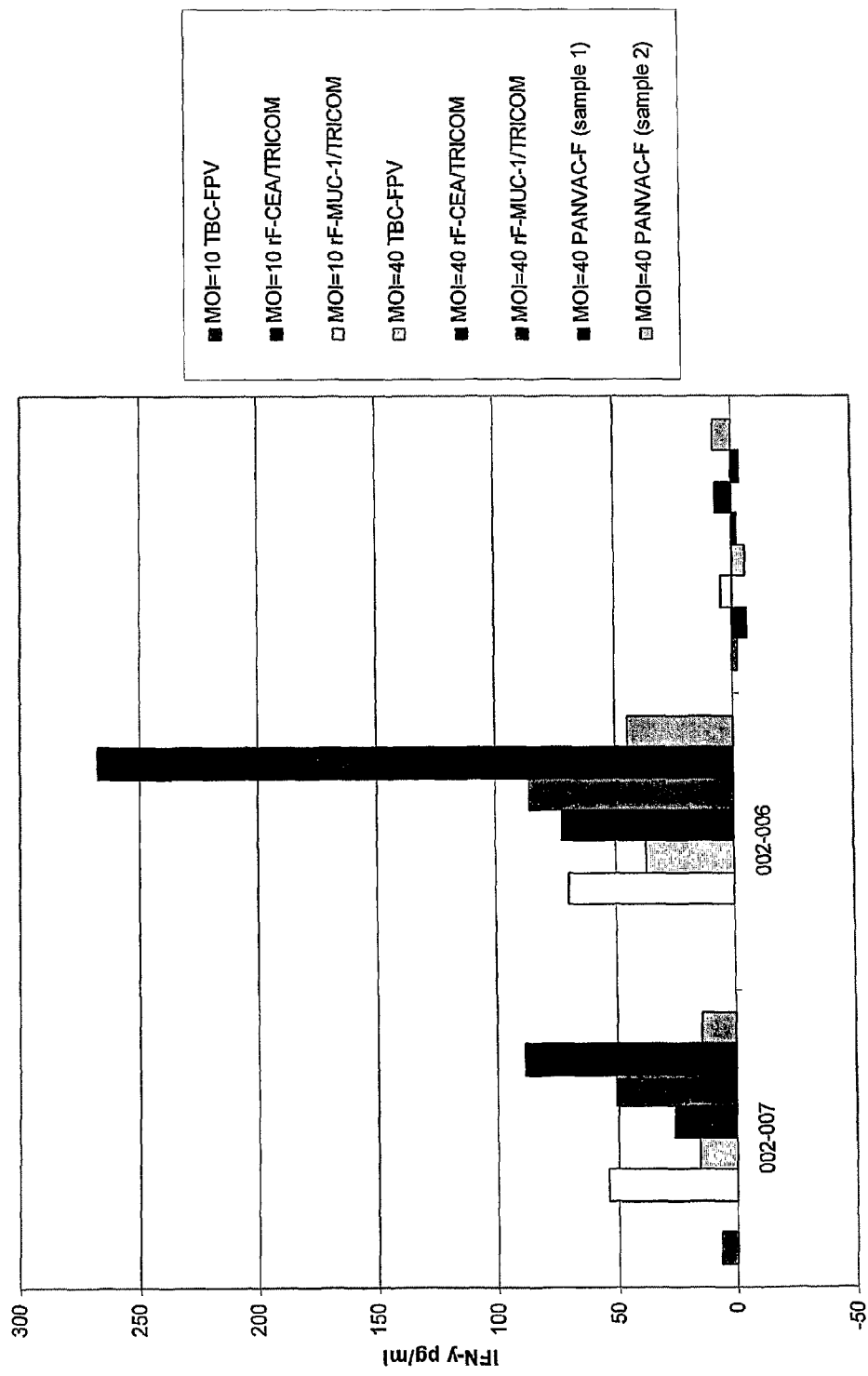
FIG. 2 is a bar graph depicting levels of IFN-γ secreted by PBMC obtained from an HLA-A2$^+$ patient (002-007) and an HLA-A2$^-$ patient (002-006) 70 days after initiation of treatment with the PANVAC-VF regimen, and by PBMC from a non-vaccinated patient (Naïve donor). PBMC were stimulated in the presence of CMMT 110/C1 cells infected with the following recombinant viruses (either at MOI=10 or MOI=40, as indicated): TBC-FPV, rF-CEA, rF-MUC-1, PANVAC-F (sample 1), and PANVAC-F (sample 2).

ELISA assays for IFN-γ assays were performed as described in Example 1 above. Undiluted culture supernatants were assayed. The results are shown in FIG. 2. Con A results are excluded because the levels of IFN-γ were too high to be measured accurately. The results for conditions in which C1R-A2 cells were used are not graphed because there was very little difference between the control and peptide-pulsed C1R-A2 samples.

As shown in FIG. 2, very little or no IFN-γ was produced by PBMC from the unvaccinated donor at all conditions tested. Neither patient #7 nor 6 samples responded to CMMT 110/C1 cells infected with TBC-FPV and rF-CEA/TRICOM when the target cells had been infected at a MOI of 10. The response to rF-MUC-1/TRICOM-infected cells was more robust. Patients #7 and 6 PBMC responded to TBC-FPV, rF-CEA/TRICOM, rF-MUC-1/TRICOM, and PANVAC-F infected cells prepared with a MOI of 40.

Responses of PBMC from vaccinated donors were generally higher in the presence of cells infected with a virus expressing a tumor antigen and were higher than those of the non-vaccinated donor, suggesting that the responses are antigen-specific. The fact that PBMC of both patients #6 and #7 exhibited responses indicate that cells of both HLA-A2$^+$ and an HLA-A2$^-$ donors can be measured in this assay.

Example 3

Comparison of Immune Responsiveness of Vaccinated and Non-vaccinated Donors

The assays using CMMT 110/C1 target cells were repeated with PBMC of patient #7, #6, and a non-vaccinated donor. In these experiments, additional conditions were tested using CMMT 110/C1 cells infected with a fowlpox virus encoding human B7.1, LFA-3, and ICAM-1 (rF-TRICOM). Cells were infected at a MOI of both 10 and 40 for all conditions tested. The following combinations of PBMC and target cell/antigen conditions were tested:
PBMCs+Media
PBMCs+Con A
PBMCs+Vaccinia Lysate
PBMCs+CMMT 110/C1
PBMCs+CMMT 110/C1 infected with TBC-FPV
PBMCs+CMMT 110/C1 infected with rF-CEA/TRICOM
PBMCs+CMMT 110/C1 infected with rF-MUC-1/TRICOM
PBMCs+CMMT 110/C1 infected with PANVAC-F (sample 1)
PBMCs+CMMT 110/C1 infected with PANVAC-F (sample 2)

ELISPOT assays were performed with cells after harvest, as described in Example 1. Once again, the vaccinia, Con A, and media controls gave the expected positive, positive, and negative signals, respectively. Spots were detected from samples for subsets of conditions with PBMC of patients #7 and #6, but no clear pattern of response was detected between samples when measured by this method.

Figure 3:
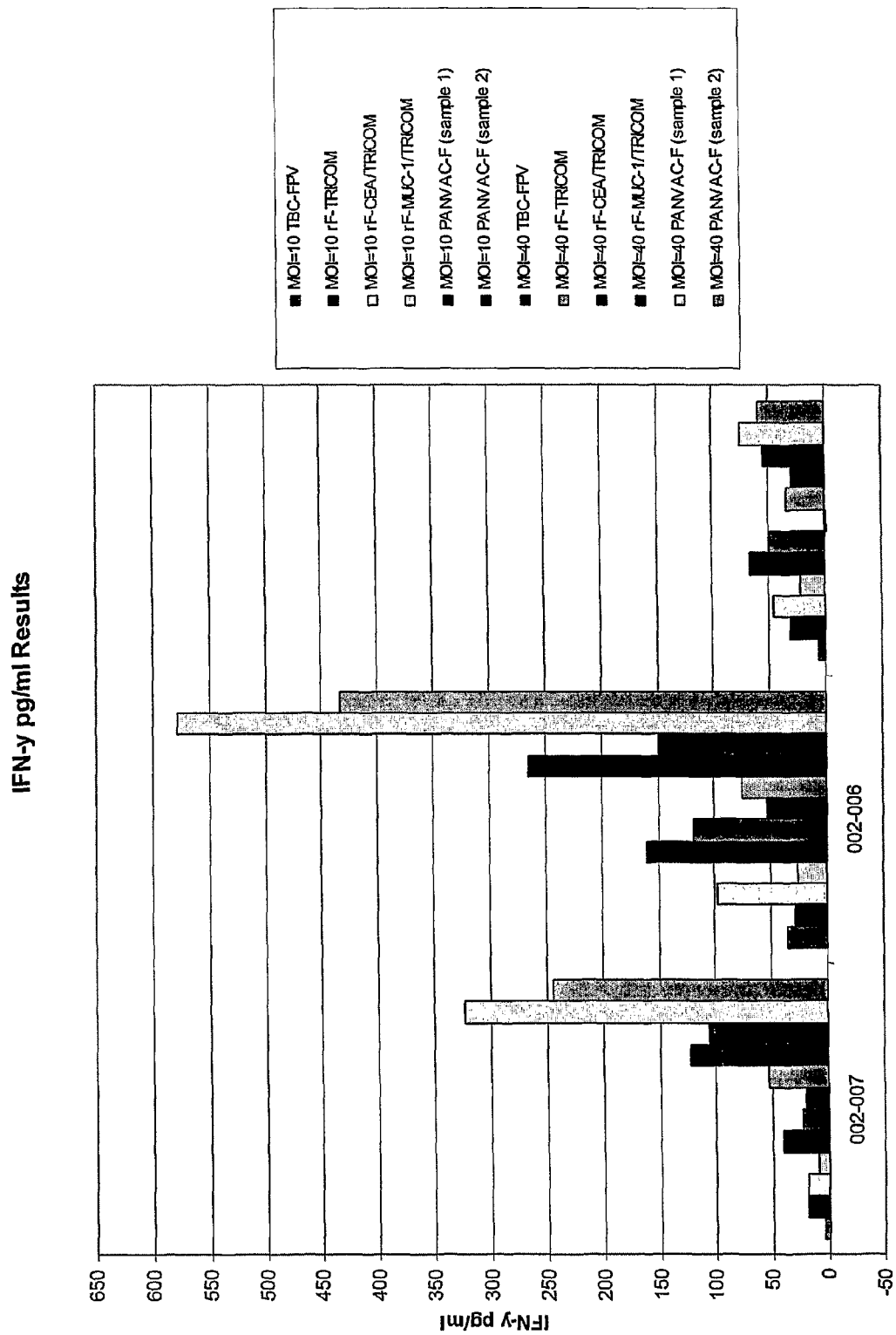
FIG. 3 is a bar graph depicting levels of IFN-γ secreted by PBMC obtained from an HLA-A2$^+$ patient (002-007) and an HLA-A2$^-$ patient (002-006) 70 days after initiation of treatment with the PANVAC-VF regimen, and by PBMC from a non-vaccinated patient (Naïve Donor). PBMC were stimulated in the presence of CMMT 110/C1 cells infected with the following recombinant viruses (either at MOI=10 or MOI=40, as indicated): TBC-FPV, rF-TRICOM, rF-CEA, rF-MUC-1, PANVAC-F (sample 1), and PANVAC-F (sample 2).

IFN-γ ELISA assays were performed with culture supernatants as described in Example 1. The results are depicted in FIG. 3, which shows that the levels of IFN-γ were higher in conditions employing CMMT 110/C1 cells infected at the higher MOI. Con A results are not plotted in FIG. 3. The order of responses under different sample conditions, ordered from highest response to lowest, was the same for both vaccinated donors: PANVAC-F (sample 1)>PANVAC-F (sample 2)>rF-CEA/TRICOM>rF-MUC-1/TRICOM>rF-TRICOM>TBC-FPV. The responses of PBMC from the non-vaccinated donor were equivalent at both MOI of 10 and 40. The low levels of IFN-γ secreted by the non-vaccinated PBMC suggested a lack of antigen-specific response in the non-vaccinated donor.

Example 4

Optimization of Incubation Time and Target:PBMC Ratios

The following assay was performed using PBMC from one vaccinated patient, #6, undergoing treatment with the PANVAC-VF regimen. This assay was designed to examine IFN-γ levels released over a one-week incubation period. Culture supernatants were collected after 6 hours, 1 day, 2 days, 3 days, 4 days, 5 days, 6 days, and 7 days. The conditions were as follows:
  PBMCs+Uninfected CMMT 110/C1
  PBMCs+CMMT 110/C1 infected with TBC-FPV
  PBMCs+CMMT 110/C1 infected with PANVAC-F (sample 1)

Figure 4:
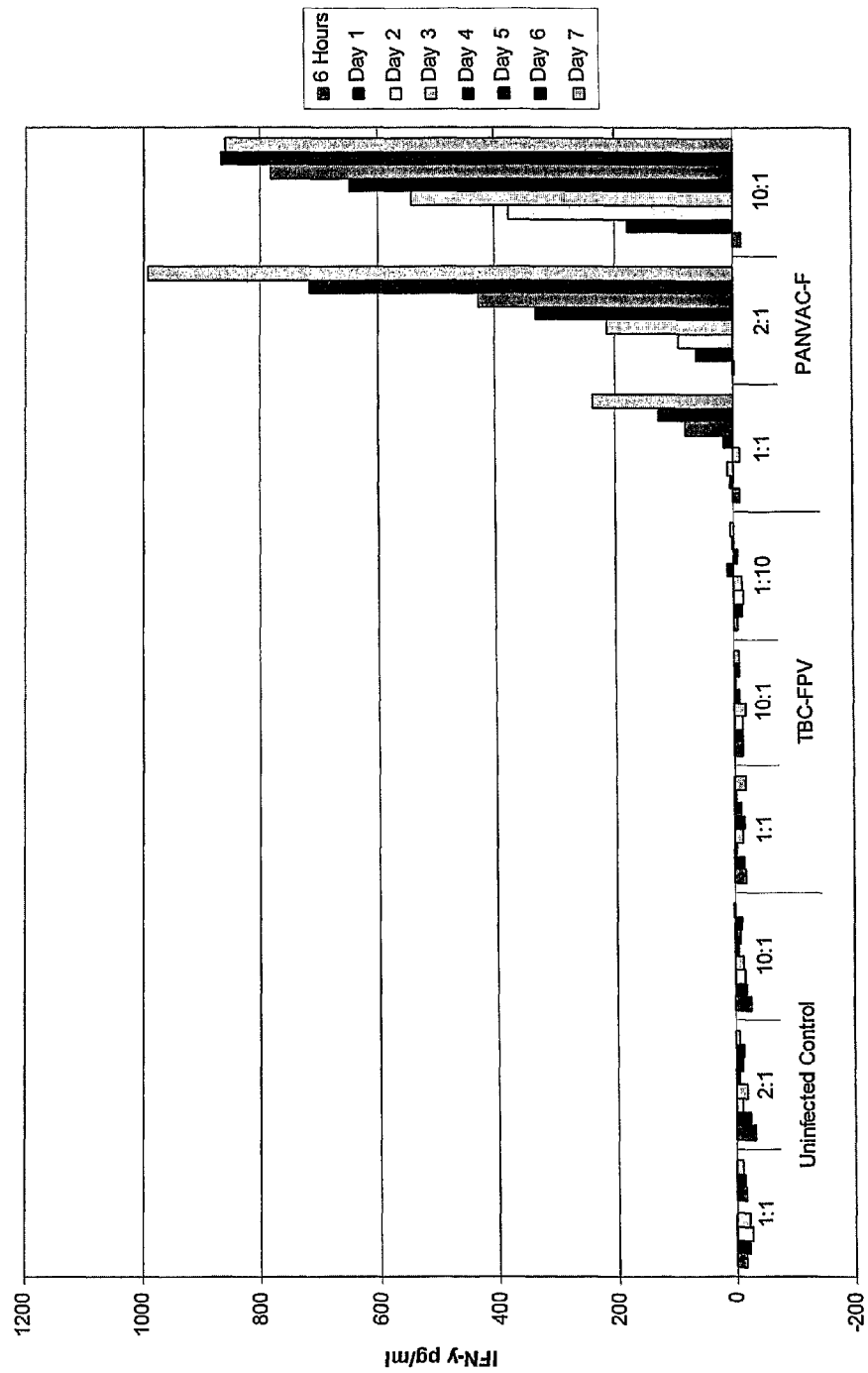
FIG. 4 is a bar graph depicting levels of IFN-γ secreted by PBMC obtained from an HLA-A2$^-$ patient (002-006) 70 days after initiation of treatment with the PANVAC-VF regimen. PBMC were stimulated in the presence of CMMT 110/C1 cells uninfected with virus or infected with TBC-FPV or PANVAC-F. Cells were incubated at ratios of 1:1, 1:2, or 1:10 CMMT 110/C1: PBMC and supernatants were sampled for IFN-γ ELISA at 6 hours, and 1, 2, 3, 4, 5, 6, and 7 days after co-culture.

In addition, three different ratios of PBMC:CMMT 110/C1 cells for each condition above were tested: 1:1; 2:1; and 10:1. All CMMT 110/C1 cells were infected at a MOI of 40. Levels of IFN-γ secretion in culture supernatants were quantitated by ELISA as described in Example 1. The results are plotted in FIG. 4, which shows that responses against uninfected and TBC-FPV were negative at all days and cell ratios tested. Responses against PANVAC-F were observed at 1:1, 2:1, and 10:1 PBMC: CMMT 110/C1 ratios. Levels of IFN-γ increased with each additional day of culture, with the highest levels observed at day 7.

Figure 5:
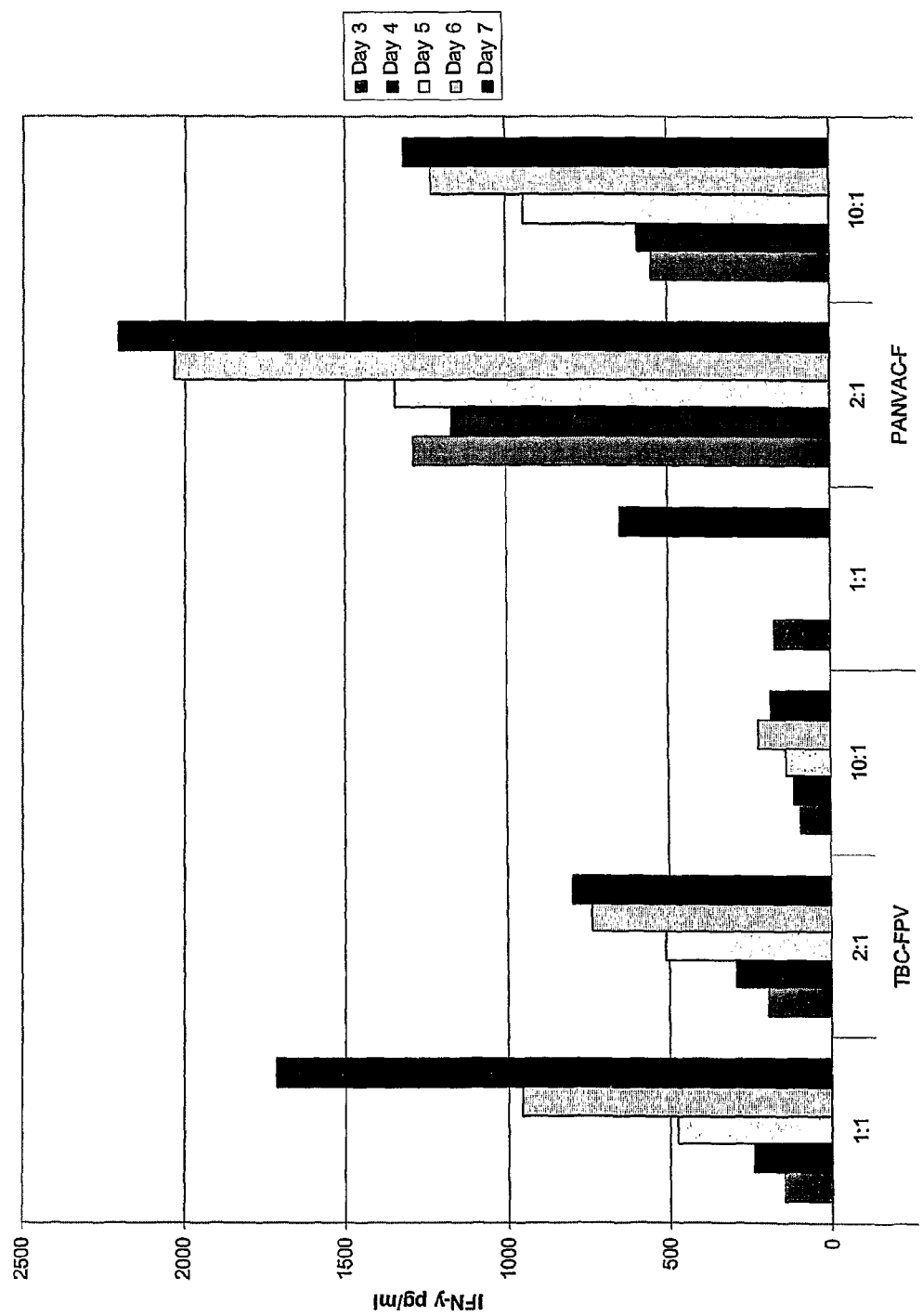
FIG. 5 is a bar graph depicting levels of IFN-γ secreted by PBMC obtained from an HLA-A2$^-$ patient (002-006) 70 days after initiation of treatment with the PANVAC-VF regimen. PBMC were stimulated in the presence of CMMT 110/C1 cells infected with TBC-FPV or PANVAC-F. Cells were incubated at ratios of 1:1, 1:2, or 1:10 CMMT 110/C1: PBMC and supernatants were sampled for IFN-γ ELISA at 3, 4, 5, 6, and 7 days after co-culture.

The assay was repeated with PBMC from the same vaccinated donor. Supernatants were collected after 3, 4, 5, 6, and 7 days of incubation and IFN-γ levels were quantitated by ELISA. The results are depicted in FIG. 5. The 1:1 ratio of cells gave the highest level of response to TBC-FPV-infected cells. The 10:1 ratio produced the lowest level of response to TBC-FPV-infected cells. Levels of responsiveness to TBC-FPV-infected cells appeared to increase over time. The 2:1 and 10:1 ratios elicited the highest levels of response to PANVAC-F-infected cells. Day 7 supernatants contained the highest levels of IFN-γ to PANVAC-F-infected cells at all three ratios.

Figure 6:
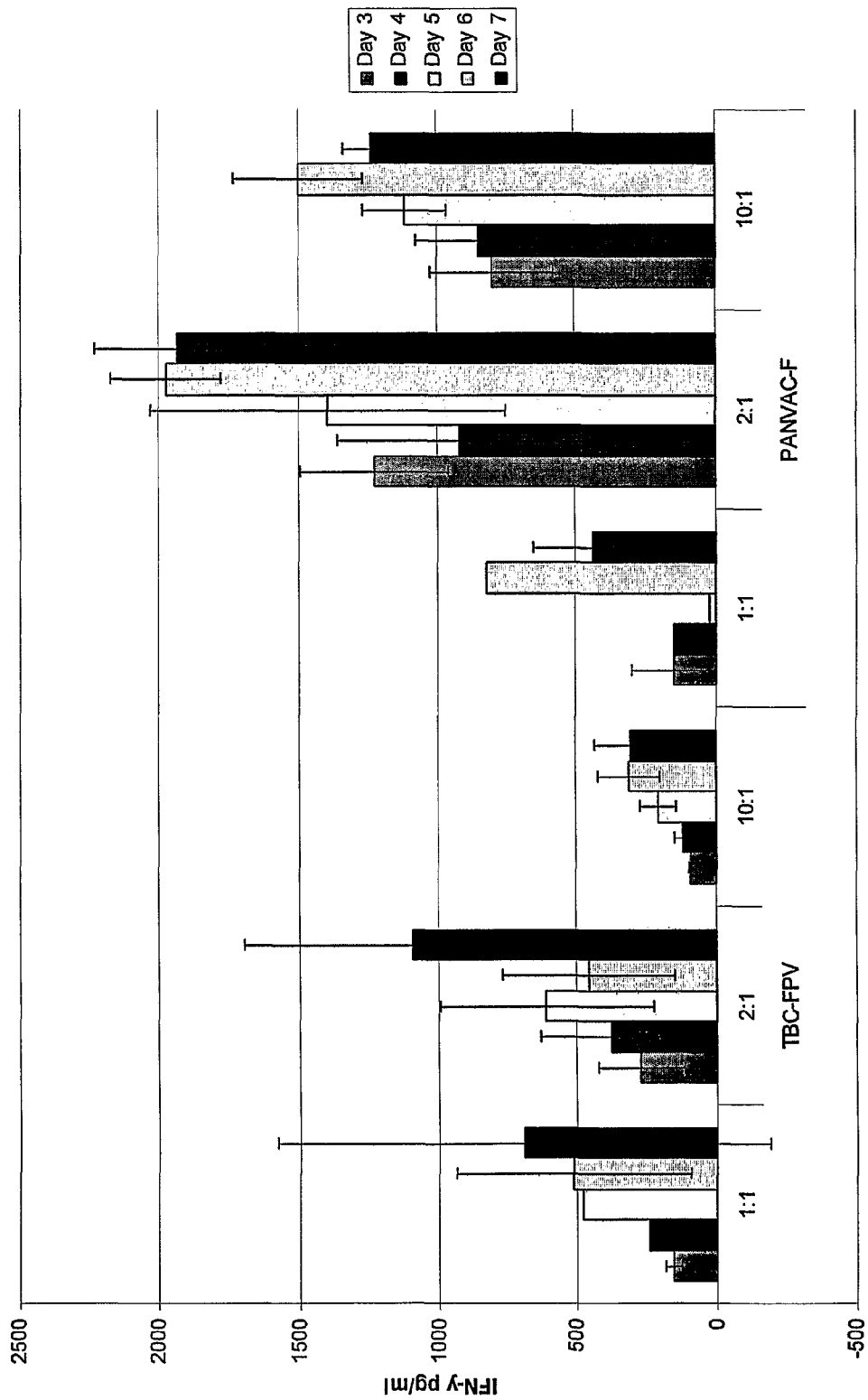
FIG. 6 is a bar graph depicting levels of IFN-γ secreted by PBMC obtained from an HLA-A2$^-$ (002-006) patient 70 days after initiation of treatment with the PANVAC-VF regimen. PBMC were stimulated in the presence of CMMT 110/C1 cells infected with TBC-FPV or PANVAC-F. Cells were incubated at ratios of 1:1, 1:2, or 1:10 CMMT 110/C1: PBMC and supernatants were sampled for IFN-γ ELISA at 3, 4, 5, 6, and 7 days after co-culture.
Figure 7:
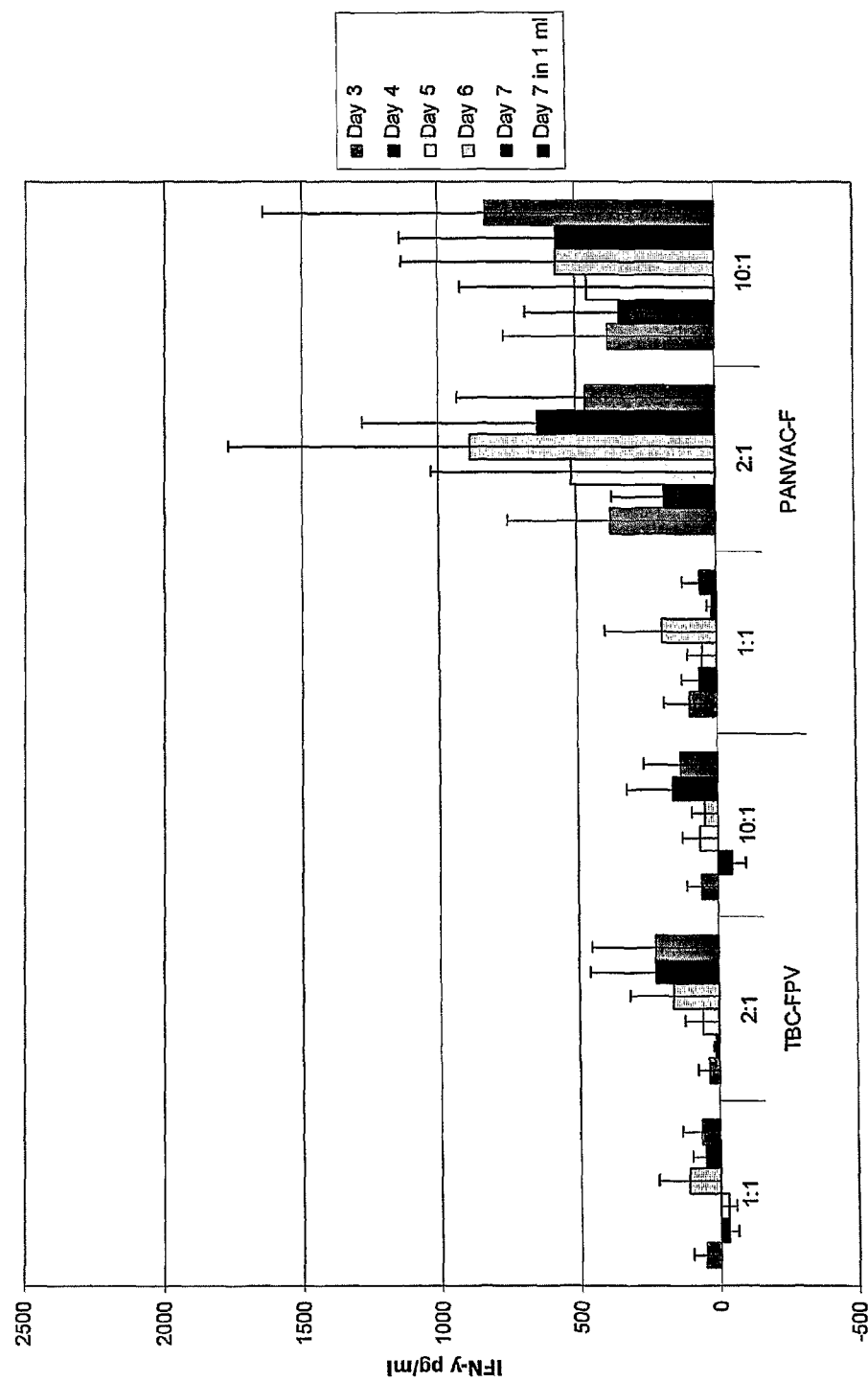
FIG. 7 is a bar graph depicting levels of IFN-γ secreted by PBMC obtained from an HLA-A2$^+$ patient (002-007) 70 days after initiation of treatment with the PANVAC-VF regimen. PBMC were stimulated in the presence of CMMT 110/C1 cells infected with TBC-FPV or PANVAC-F. Cells were incubated at ratios of 1:1, 1:2, or 1:10 CMMT 110/C1: PBMC and supernatants were sampled for IFN-γ ELISA at 3, 4, 5, 6, and 7 days after co-culture.
Figure 8:
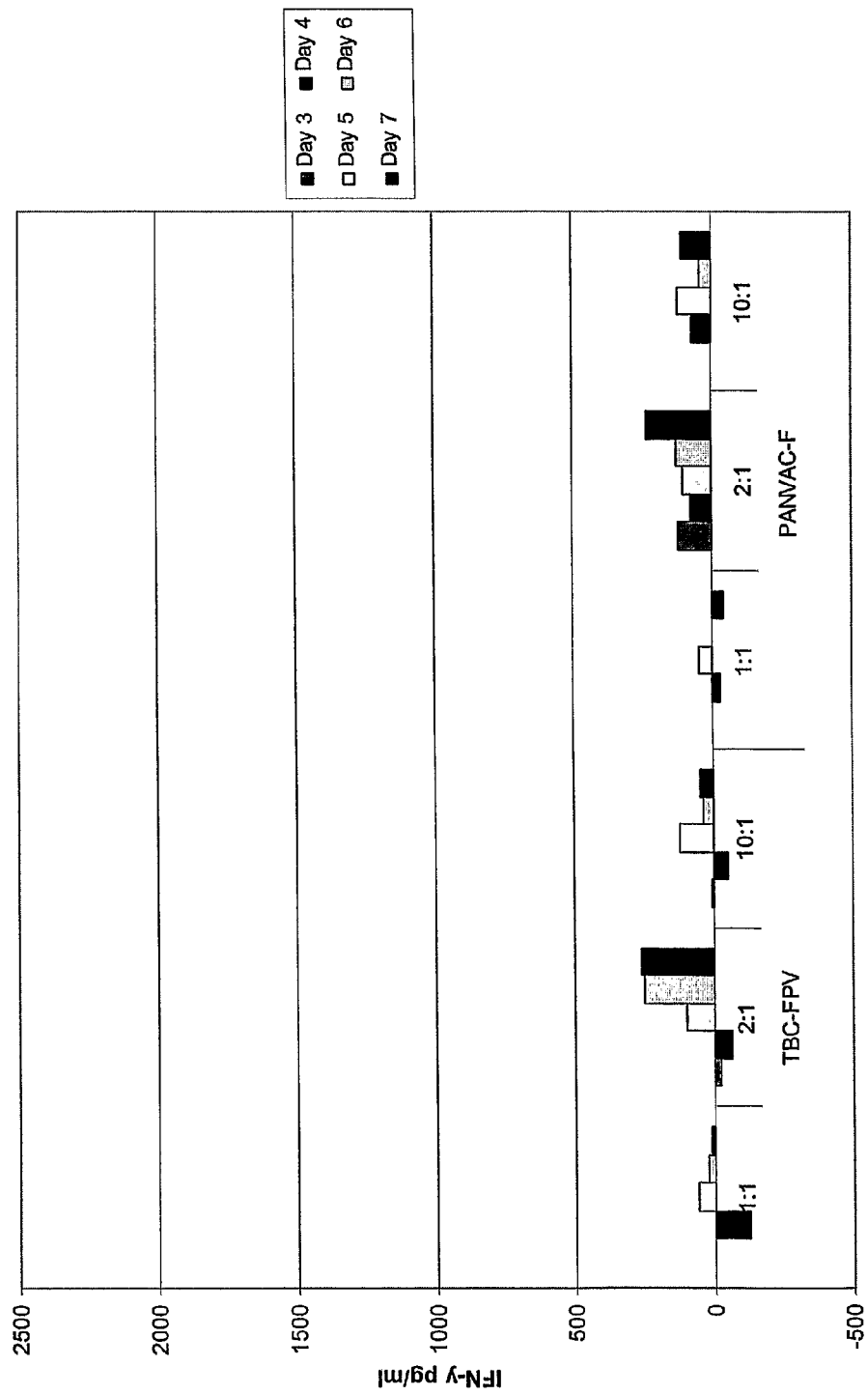
FIG. 8 is a bar graph depicting levels of IFN-γ secreted by PBMC obtained from an unvaccinated patient (Naïve Donor). PBMC were stimulated in the presence of CMMT 110/C1 cells infected with TBC-FPV or PANVAC-F. Cells were incubated at ratios of 1:1, 1:2, or 1:10 CMMT 10/C1: PBMC and supernatants were sampled for IFN-γ ELISA at 3, 4, 5, 6, and 7 days after co-culture.

The assay conditions were repeated with PBMC from the same vaccinated donor, #6, from a second vaccinated donor, #7, and a non-vaccinated donor. CMMT 110/C1 cells were infected at a MOI of 40 with either TBC-FPV or PANVAC-F. Supernatants were collected after 3, 4, 5, 6, and 7 days of incubation. Levels of IFN-γ secretion in culture supernatants were quantitated by ELISA. The results for patients #6, 7, and non-vaccinated PBMC are depicted in FIGS. 6, 7, and 8, respectively. The standard curves for this ELISA did not produce accurate values, therefore the concentrations shown in FIGS. 6, 7, and 8 may not reflect the actual concentration, but trends are apparent. The relatives levels of IFN-γ observed for the different conditions in FIG. 6 for patient #6 are similar to those obtained in FIG. 5. In general, levels of IFN-γ increased with each day of incubation. PANVAC-F induced levels of IFN-γ higher than those induced by TBC-FPV, indicative of a specific response to antigens expressed by PANVAC-F. This trend was also observed in the assays with PBMC from patient 7 (FIG. 7). Levels of IFN-γ produced by PBMC from the non-vaccinated donor were low at all conditions tested (FIG. 8).

Example 5

Identification of Responsive Cell Subsets

In order to examine the cell types responsible for IFN-γ production in response to stimulation with CMMT 110/C1 cells, PBMC from two PANVAC-vaccinated donors (patient #6 and #7) and one non-vaccinated donor, were separated into subsets by cell type and assayed for responsiveness to incubation with PANVAC-F or TBC-FPV-infected CMMT 110/C1 cells. Dynal Negative Isolation kits were used to prepare subsets. The subsets analyzed were total PBMC, CD3$^+$, CD4$^+$, CD8$^+$, and NK$^+$ cells. Incubations were performed with a ratio of 10:1 cell subsets: CMMT 110/C1 cells using $5\times10^5:5\times10^4$ cells due to low numbers of cells recovered after separation. Supernatants were collected after 3 and 6 days in culture.

Figure 9:
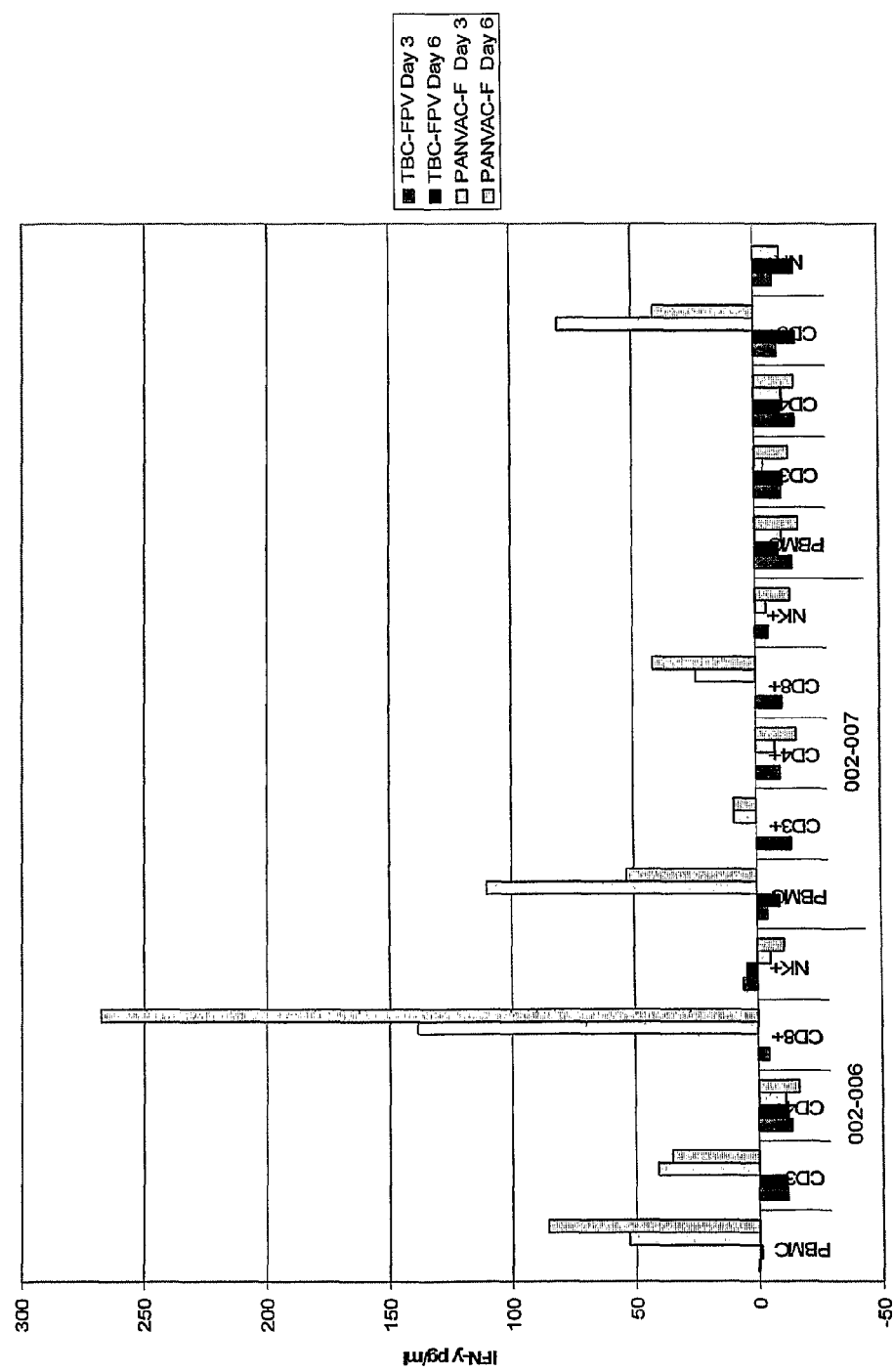
FIG. 9 is a bar graph depicting levels of IFN-γ secreted by PBMC and subsets of cells thereof in response to stimulation in the presence of CMMT 110/C1 cells infected with TBC-FPV or PANVAC-F. Two sets of PBMC used in this experiment were obtained from an HLA-A2$^+$ patient (002-007) and an HLA-A2$^-$ patient (002-006) 70 days after initiation of treatment with the PANVAC-VF regimen. The third set was obtained from a non-vaccinated patient (Naïve Donor). The cell subsets tested in this assay were PBMC, CD3$^+$, CD4$^+$, CD8$^+$, and NK$^+$ cells.

The subsets of cells which elicited an IFN-γ response by cells from vaccinated donors were PBMC (as expected), CD8$^+$ cells, and CD3$^+$ cells from samples exposed to PANVAC-F-infected CMMT 110/C1 cells (FIG. 9). CD8$^+$ cells from patient #6 elicited the highest levels, followed by PBMC and CD3$^+$ cells of this patient. PBMC from patient #7 elicited the highest IFN-γ response, followed by CD8$^+$ and CD3$^+$ cells. All values obtained for the unvaccinated donor cells were negative, except for positive responses from CD8$^+$ cells exposed to PANVAC-F-infected CMMT 110/C1 cells. The reason for this response is unknown.

Example 6

Optimization of Plate Size and Cell Number and Comparison of Patient Responsiveness Before and After Vaccination The non-restricted assay was repeated with a 24-well plate rather than a 48-well plate (as used in the assays described in Examples 1-5). A 10:1 ratio of PBMC: CMMT 110/C1 cells were used, with cell quantities of $1\times10^6$ and $1\times10^5$. Supernatant was removed for IFN-γ quantitation after 3 days of incubation.

Figure 10:
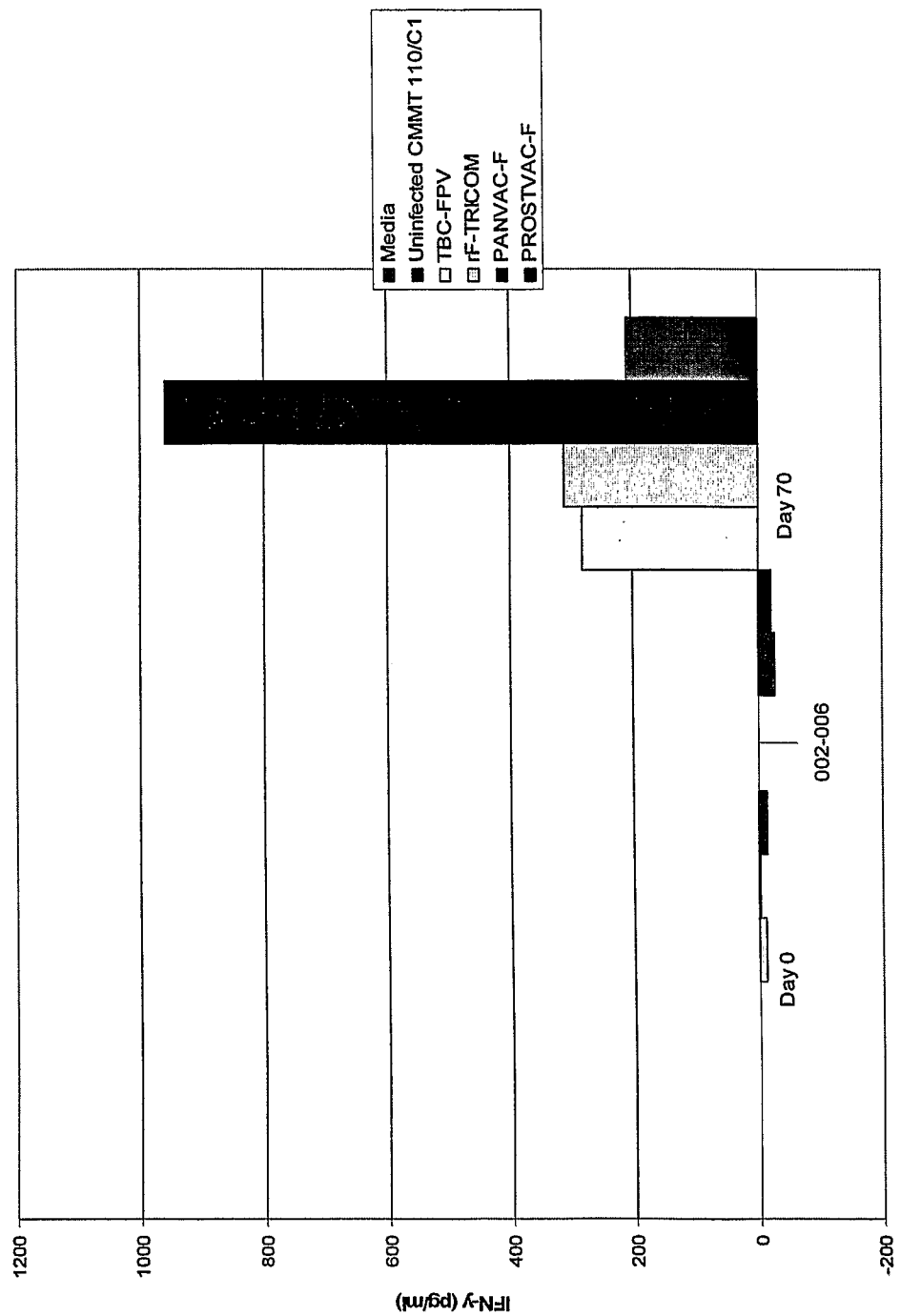
FIG. 10 is a bar graph depicting levels of IFN-γ secreted by PBMC from an HLA-A2$^-$ (002-006) patient 0 and 70 days after initiation of treatment with the PANVAC-VF regimen.

Patient responsiveness to treatment with the PANVAC-VF regimen was also examined in this assay by comparing PBMC obtained from a patient (#6) at day 0 or treatment and day 70 of treatment. Another specificity control was added by adding a condition in which CMMT 110/C1 cells were infected with PROSTVAC®-F. (PROSTVAC®-F is a recombinant fowlpox that expresses the TAA prostate-specific antigen (PSA) and TRICOM and does not express the TAAs present in PANVAC-VF). The results are shown in FIG. 10. There were no IFN-γ responses in any of the day 0 conditions. The day 70 PBMC from this patient also showed no response in the media and uninfected CMMT 110/C1 conditions, and small responses in the TBC-FPV, rF-TRICOM and PROSTVAC®-F conditions, possibly due to responses against fowlpox antigens. The day 70 PBMC exhibited a much greater (~5 times greater) response to PANVAC-F than to any other conditions, suggestive of a TAA-specific response.

Example 7

Patient Responses at Various Time Points After Treatment

PBMC samples from two patients treated with the PANVAC-VF regimen, patient #7 and patient #11 (001-011; an HLA-A2$^-$ patient), were examined. PBMC taken 28, 42, 70 days, 70 days plus one month, 70 days plus 2 months, and 70 days plus 3 months after initiation of the PANVAC-VF regimen were tested. PBMC from these time points were incubated in the following combinations: this was the order in which to do the assay, depending on the number of cells recovered. At some timepoints not all conditions were tested.

Each patient PBMCs (from all time-points)+CMMT 110/C1 infected with PANVAC-F

Each patient PBMCs (from all time-points)+CMMT 110/C1 infected with rF-TRICOM

Each patient PBMCs (from all time-points)+CMMT 110/C1 infected with PROSTVAC®-F

Each patient PBMCs (from all time-points)+CMMT 110/C1 infected with rF-IF

Each patient PBMCs (from all time-points)+Uninfected CMMT 110/C1 cells

Each patient PBMCs (from all time-points)+CMMT 110/C1 infected with TBC-FPV

PROSTVAC®-F-infected CMMT 110/C1 cells were used as a control. Sets of target cells infected with rF-IF, a recombinant fowlpox virus expressing an influenza antigen, were also used. Cells were incubated in 24-well plates at 10:1 ratios. Supernatants were collected after 3 days in culture and IFN-γ levels were quantitated by ELISA.

As shown in FIG. 11, PBMC from patient #6 exhibited the highest responses to PANVAC-F-infected target cells at all time points examined, releasing quantities of IFN-γ 1.5-4 times higher than those at all other conditions. The cells did not respond to uninfected and TBC-FPV-infected targets. Low levels of responses were seen to targets infected with rF-TRICOM, rF-IF, and PROSTVAC®-F at day 70 and month 3. Responses by patient #11 PBMC were much lower than those of patient #6 PBMC, with the highest responses appearing at day 42, day 70, and 70 days plus 2 months in cells stimulated with PANVAC-F-infected targets. Lower levels of responses to rF-TRICOM were also observed. Overall, the most robust responses in both patients were to cells infected with PANVAC-F.

PBMC samples from two more patients receiving treatment with the PANVAC regimen, patients #1 and #11 (both of whom are HLA-A2), were examined in the non-restricted assay. The assay was performed in a 24-well plate with a 10:1 ratio of cells. PBMCs from the following days after treatment were used in this assay:

i. #1-Day 0, 14, 28, 42, 70, Month #1RD and Month #2
ii. #11-Day 14, 28, 42

PBMC were incubated with CMMT 110/C1 cells as follows, where numbers of patient PBMC cells permitted:

PBMCs (from all time-points)+CMMT 110/C1 infected with PANVAC-F

PBMCs (from all time-points)+CMMT 110/C1 infected with rF-TRICOM

PBMCs (from all time-points)+CMMT 110/C1 infected with PROSTVAC®-F

PBMCs (from all time-points)+Con A in media at 2.5 μg/ml

PBMCs (from all time-points)+Uninfected CMMT 110/C1 cells

Con A-containing samples exhibited very high levels of IFN-γ (~800 pg/ml or greater) in many assay conditions and are not plotted on FIG. 12. Patient #1's cells were not healthy once thawed, so for many time points, there were only enough cells to perform one assay condition. As shown in FIG. 12, PBMC of all patients exhibited the greatest responsiveness to PANVAC-F infected cells at many of the time points tested. No PANVAC-F-responsiveness was observed at day 0 in any of the samples.

Example 8

Responsiveness to Target Cells Expressing Tumor Antigens

The following assay was performed with PBMC collected 70 days after treatment with the PANVAC-VF regimen was initiated in patients #7 and #6. PBMC of a non-vaccinated donor were also tested. The non-restricted assay was performed in 24-well plates with a 10:1 ratio of cells ($1 \times 10^6$:$1 \times 10^5$). The following conditions were used:

PBMCs+CMMT 110/C1 infected with PANVAC-F

Each patient PBMCs+CMMT 110/C1 infected with rF-TRICOM

Each patient PBMCs+CMMT 110/C1 infected with rF-CEA(6D)

Each patient PBMCs+CMMT 110/C1 infected with rF-MUC-1

Each patient PBMCs+CMMT 110/C1 infected with rF-CEA(6D)/TRICOM

Each patient PBMCs+CMMT 110/C1 infected with rF-MUC-1/TRICOM

Supernatants were removed after three days and IFN-γ levels were quantitated. The results are depicted in FIG. 13. No responses were observed in PBMC from the non-vaccinated individual. All samples from patients #6 and #7 responded in this assay. rF-CEA(6D)/TRICOM elicited the highest response. PANVAC-F elicited the next-highest response. rF-CEA (6D) elicited the next highest response. rF-MUC-1 responses were low in these assays, which was not expected.

Example 9

Analysis of Additional Patient PBMC Responses to Tumor Antigens

In this assay, PBMC from three different patients (#12, #13, and #14) taken 0, 14, 28, 37, 42, and 63 days (or a subset thereof) after initiation of PANVAC-VF treatment were incubated under the following conditions:

Each patient PBMCs (from all time-points)+CMMT 110/C1 infected with PANVAC-F

Each patient PBMCs (from all time-points)+CMMT 100/C1 infected with rF-TRICOM

Each patient PBMCs (from all time-points)+CMMT 110/C1 infected with PROSTVAC®-F

Each patient PBMCs (from all time-points)+Con A in media at 2.5 μg/ml

Each patient PBMCs (from all time-points)+Uninfected CMMT 110/C1 cells

The results are depicted in FIG. 14. Patient #13 PBMC exhibited low/no responses under all conditions. High levels of IFN-γ secretion were observed in samples from patient #13 in response to cells infected with all three viruses and in response to ConA stimulation. Patient #14 PBMC responded to Con A at time points from days 42 and 63 only, and did not exhibit responses to infected cells at any time points.

Example 10

Long-Range Responsiveness in Vaccinated Individuals

In this assay, cells from patient 7 undergoing PANVAC-VF treatment were incubated with CMMT 110/C1 cells infected with various viral recombinants. PBMC samples obtained from the patient at various times after initiation of treatment with the PANVAC-VF regimen were tested. PBMC isolated from patient #7 at 4, 5, 7, and 9 months after initiation of PANVAC-VF treatment responded, whereas cells from 70 days, 6 months, and 8 months after treatment did not (FIG. 15). PANVAC-F elicited the greatest response (in those samples from the time point in which a response was observed). The responses elicited by PROSTVAC®-F and rF-TRICOM were roughly equivalent, suggesting that the cells are responding to fowlpox rather than PSA expression.

A number of embodiments of the invention have been described. Nevertheless, it will be understood that various modifications may be made without departing from the spirit and scope of the invention. Accordingly, other embodiments are within the scope of the following claims.

What is claimed is:

1. A method for detecting an antigen-specific hematopoietic cell in a biological sample, which method comprises:
   (a) providing a biological sample comprising a hematopoietic cell of a first species;
   (b) providing a target cell of a second species, wherein the second species is different from the first species, wherein the second species is a macaque species, wherein the target cell comprises an antigen and wherein previous determination of the target cell MHC genotype is not required;
   (c) contacting the target cell with the biological sample; and
   (d) detecting an immune activation marker in the sample in an MHC-non-restricted manner,
   wherein an increase in expression of the immune activation marker in the sample, relative to a control, is an indication that the sample comprises an antigen-specific hematopoietic cell;
   wherein a cell identical to the target cell but lacking the antigen does not stimulate expression of the immune activation marker in hematopoietic cells of the first species, and
   wherein the immune activation marker is selected from the group consisting of B7.1, B7.2, CD 152 (CTLA-4), CD28, CD40, CD40 ligand (CD40L), and CD69.

2. The method of claim 1, wherein the antigen is a tumor-associated antigen (TAA) or a microbial antigen.

3. The method of claim 2, wherein the antigen is a carcinoembryonic antigen (CEA) or a mucin-1 (MUC-1).

4. The method of claim 2, wherein the antigen is a viral antigen or a bacterial antigen.

5. The method of claim 1, wherein the biological sample comprises peripheral blood mononuclear cells (PBMC).

6. The method of claim 1, wherein the target cell is infected with a virus that encodes the antigen.

7. The method of claim 6, wherein the virus is a DNA virus or a poxvirus.

8. The method of claim 6, wherein the virus encodes B7.1, LFA-3, and ICAM-1.

9. The method of claim 1, wherein the target cell is transfected with a nucleic acid that encodes the antigen.

10. The method of claim 1, wherein the sample and the target cell are incubated together at step (c) for at least 24 hours.

11. The method of claim 1, wherein the sample and the target cell are incubated together at step (c) for a period of time that is less than 7 days.

12. A method for detecting an antigen-specific hematopoietic cell in a biological sample, which method comprises:
 (a) providing a biological sample comprising a hematopoietic cell of a first species;
 (b) providing a target cell of a second species, wherein the second species is different from the first species, wherein the second species is a macaque species, wherein the target cell comprises an antigen and wherein previous determination of the target cell MHC genotype is not required;
 (c) contacting the target cell with the biological sample; and
 (d) detecting an immune activation marker or activity in the sample in an MHC-non-restricted manner,
 wherein an increase in expression of the immune activation marker or activity in the sample, relative to a control, is an indication that the sample comprises an antigen-specific hematopoietic cell;
 wherein a cell identical to the target cell but lacking the antigen does not stimulate expression of the immune activation marker or activity in hematopoietic cells of the first species,
 wherein the target cell is infected with a virus that encodes the antigen, and
 wherein the virus further encodes one or more costimulatory molecules of the first species.

13. The method of claim 12, wherein the costimulatory molecules comprise one or more of the group consisting of B7.1, LFA-3, and ICAM-1.

14. The method of claim 12, wherein the antigen is a tumor-associated antigen (TAA), a viral antigen, or a bacterial antigen.

15. The method of claim 14, wherein the antigen is a carcinoembryonic antigen (CEA) or a mucin-1 (MUC-1).

16. The method of claim 12, wherein the biological sample comprises peripheral blood mononuclear cells (PBMC).

17. The method of claim 12, wherein the virus is a DNA virus or a poxvirus.

18. The method of claim 12, wherein the sample and the target cell are incubated together at step (c) for at least 24 hours.

19. The method of claim 12, wherein the sample and the target cell are incubated together at step (c) for a period of time that is less than 7 days.

20. A method for detecting an antigen-specific hematopoietic cell in a biological sample, which method comprises:
 (a) providing a biological sample comprising a hematopoietic cell of a first species;
 (b) providing a target cell of a second species, wherein the second species is different from the first species, wherein the second species is a macaque species, wherein the target cell comprises an antigen and wherein previous determination of the target cell MHC genotype is not required;
 (c) contacting the target cell with the biological sample in an MHC-non-restricted manner; and
 (d) detecting an immune activation marker or activity in the sample,
 wherein an increase in expression of the immune activation marker or activity in the sample, relative to a control, is an indication that the sample comprises an antigen-specific hematopoietic cell;
 wherein a cell identical to the target cell but lacking the antigen does not stimulate expression of the immune activation marker or activity in hematopoietic cells of the first species, and
 wherein the target cell is a cell of cell line CMMT 110/C1.

21. The method of claim 20, wherein the antigen is a tumor-associated antigen (TAA), a viral antigen, or a bacterial antigen.

22. The method of claim 21, wherein the antigen is a carcinoembryonic antigen (CEA) or a mucin-1 (MUC-1).

23. The method of claim 20, wherein the biological sample comprises peripheral blood mononuclear cells (PBMC).

24. The method of claim 20, wherein the target cell is infected with a virus that encodes the antigen.

25. The method of claim 24, wherein the virus is a DNA virus or a poxvirus.

26. The method of claim 24, wherein the virus encodes B7.1, LFA-3, and ICAM-1.

27. The method of claim 20, wherein the target cell is transfected with a nucleic acid that encodes the antigen.

28. The method of claim 20, wherein the sample and the target cell are incubated together at step (c) for at least 24 hours.

29. The method of claim 20, wherein the sample and the target cell are incubated together at step (c) for a period of time that is less than 7 days.

* * * * *